(12) United States Patent
Nakamura et al.

(10) Patent No.: US 11,250,934 B2
(45) Date of Patent: Feb. 15, 2022

(54) TEST SERVER, TEST METHOD, AND TEST SYSTEM

(71) Applicant: SONY CORPORATION, Tokyo (JP)

(72) Inventors: Tomohiko Nakamura, Tokyo (JP); Naoki Morimoto, Tokyo (JP)

(73) Assignee: SONY CORPORATION, Tokyo (JP)

( * ) Notice: Subject to any disclaimer, the term of this patent is extended or adjusted under 35 U.S.C. 154(b) by 720 days.

(21) Appl. No.: 15/303,060

(22) PCT Filed: Mar. 9, 2015

(86) PCT No.: PCT/JP2015/001252
§ 371 (c)(1),
(2) Date: Oct. 10, 2016

(87) PCT Pub. No.: WO2015/159477
PCT Pub. Date: Oct. 22, 2015

(65) Prior Publication Data
US 2017/0024521 A1    Jan. 26, 2017

(30) Foreign Application Priority Data

Apr. 18, 2014  (JP) .............................. JP2014-086769

(51) Int. Cl.
*G16H 10/60* (2018.01)
*G16H 40/63* (2018.01)
(Continued)

(52) U.S. Cl.
CPC .............. *G16H 10/60* (2018.01); *G16H 40/63* (2018.01); *G16Z 99/00* (2019.02); *H04L 67/12* (2013.01); *A61B 5/00* (2013.01); *A61B 5/0022* (2013.01)

(58) Field of Classification Search
CPC combination set(s) only.
See application file for complete search history.

(56) References Cited

U.S. PATENT DOCUMENTS

2003/0004906 A1 * 1/2003 Lapointe et al.
2009/0012716 A1 * 1/2009 Urdea et al. ............ G06F 19/00
(Continued)

FOREIGN PATENT DOCUMENTS

JP        2002-117139 A      4/2002
JP        2002117139 A  *    4/2002  ............ G06F 17/60
(Continued)

*Primary Examiner* — Michael Tomaszewski
*Assistant Examiner* — William T. Monticello
(74) *Attorney, Agent, or Firm* — Chip Law Group

(57) ABSTRACT

A test server includes a communication unit and a control unit. The communication unit communicates with a plurality of communication terminals via a network. Each communication terminal is connectable to a test device capable of executing a test on presence or absence of a disease and is capable of inputting a diagnosis on the presence or absence of the disease. The diagnosis is related to the test and made by a doctor. The control unit acquires at least one of a result of the test and the diagnosis as a test information item from each communication terminal via the communication unit, causes a storage unit to store the plurality of acquired test information items, performs statistical processing on the plurality of stored test information items, and causes the communication unit to return a result of the statistical processing according to a demand given from each communication terminal.

7 Claims, 19 Drawing Sheets

|  | Disease | Non-Disease |  |  |  |
|---|---|---|---|---|---|
| Test positive | True positive a | False positive c | Positive a+c | Positive predictive value a/(a+c) | Positive rate (a+c)/(a+b+c+d) |
| Test negative | False negative b | True negative d | Negative b+d | Negative predictive value d/(b+d) | Negative rate (b+d)/(a+b+c+d) |
|  | Number of diseases a+b | Number of non-diseases c+d | Total number a+b+c+d |  |  |
|  | Sensitivity a/(a+b) | Specificity d/(c+d) |  | Accuracy (a+d)/(a+b+c+d) |  |
|  | Prevalence rate (a+b)/(a+b+c+d) |  |  |  |  |

(51) Int. Cl.
    *G16Z 99/00* (2019.01)
    *H04L 29/08* (2006.01)
    *A61B 5/00* (2006.01)

(56) References Cited

U.S. PATENT DOCUMENTS

2011/0311998 A1* 12/2011 Zeng
2014/0072987 A1*  3/2014 Ruddock et al.
2014/0342936 A1  11/2014 Rubbo et al.
2015/0338415 A1* 11/2015 Hund et al. ............. G06F 19/00

FOREIGN PATENT DOCUMENTS

| JP | 2009-005940 A |   | 1/2009 |               |
|----|---------------|---|--------|---------------|
| JP | 2009005940    | * | 1/2009 | ........... A61B 5/00 |
| JP | 2009-095649 A |   | 5/2009 |               |
| JP | 2012-508383 A |   | 4/2012 |               |
| JP | 2013-093019 A |   | 5/2013 |               |
| JP | 2013093019    | * | 5/2013 | ........... G06Q 50/24 |
| WO | 2012/033771 A2 |  | 3/2012 |               |
| WO | WO 2014/039446 | * | 9/2013 |              |

* cited by examiner

|  | Disease | Non-Disease |  |  |  |
|---|---|---|---|---|---|
| Test positive | True positive a | False positive c | Positive a+c | Positive predictive value a/(a+c) | Positive rate (a+c)/(a+b+c+d) |
| Test negative | False negative b | True negative d | Negative b+d | Negative predictive value d/(b+d) | Negative rate (b+d)/(a+b+c+d) |
|  | Number of diseases a+b | Number of non-diseases c+d | Total number a+b+c+d |  |  |
|  | Sensitivity a/(a+b) | Specificity d/(c+d) |  | Accuracy (a+d)/(a+b+c+d) |  |
|  | Prevalence rate (a+b)/(a+b+c+d) |  |  |  |  |

FIG.1

| Instrument ID | Patient ID | Sample ID | Date of test | Address, country | Gender | Age | Test result | Diagnosis of doctor | Disease ID | Test method ID | Elapsed time |
|---|---|---|---|---|---|---|---|---|---|---|---|

FIG.5

TEST SERVER, TEST METHOD, AND TEST SYSTEM

CROSS REFERENCE TO RELATED APPLICATIONS

This application is a U.S. National Phase of International Patent Application No. PCT/JP2015/001252 filed on Mar. 9, 2015, which claims priority benefit of Japanese Patent Application No. JP 2014-086769 filed in the Japan Patent Office on Apr. 18, 2014. Each of the above-referenced applications is hereby incorporated herein by reference in its entirety.

TECHNICAL FIELD

The present technology relates to a test system, a test server and a test system being capable of performing statistical processing of test information items.

BACKGROUND ART

Tests performed in medical care recently have been increasingly important in carrying out treatment of patients. Many test devices, test kits, and test methods are developed for clinical tests.

A test system can also be established as a network compatible client server system.

For example, in Patent Document 1, an intelligence module 105 configured by a computer, for example, receives patient test results from a data acquisition module such as a test system 150 through a direct connection or over a network 140. The intelligence module executes a disease classification process for analyzing the patient test results to determine whether a patient sample is associated with an inflammatory bowel disease or a clinical subtype thereof. The determination made by the process is then provided to a client system 130.

Patent Document 1: Japanese Patent Application Laid-open No. 2012-508383

SUMMARY

Problem to be Solved

An object of the present technology to provide a test server, a test method, and a test system that improve a clinical test or treatment in various aspects such as quality and cost.

Means for Solving the Problem

In order to achieve the object described above, according to an embodiment of the present technology, there is provided a test server including: a communication unit that communicates with a plurality of communication terminals via a network, the plurality of communication terminals each being capable of inputting a test result on the presence or absence of the disease and a diagnosis result about the presence or absence of the disease being related to the test and made by a doctor; and a control unit that acquires a test information item including at least the test result and the diagnosis result from the plurality of communication terminals via the communication unit, causes a storage unit to store the plurality of acquired test information items therein, calculates at least one of a sensitivity and a specificity of the test by statistical processing of the plurality of stored test information items, and causes the communication unit to respond to a result of the statistical processing according to a demand given from each of the communication terminals.

The test information items further include patient attribute information, and the control unit may be configured to calculate at least one of a sensitivity and a specificity of the test by statistical processing of the test information items that satisfy predesignated attributes.

The test information items include quantized test data items as the test result, and the control unit may group the test data items for each attribute of the patient, calculate a sensitivity and a specificity by changing a threshold value for splitting into the presence or absence of the disease, and calculate the threshold value based on the sensitivity and the specificity.

The control unit may compare at least one of the sensitivity and the specificity of a plurality types of tests performed on the same test subject, and determine a superior type of the test for the test subject.

The test information items include quantized test data items as the test results, and the control unit may group the test data items for each attribute of the patient, calculate a sensitivity and a specificity by changing a threshold value for splitting into the presence or absence of the disease, and calculate a best threshold value.

The control unit may calculate at least one of a positive likelihood ratio and a negative likelihood ratio, and cause the communication unit to respond thereto.

Effects

As described above, according to the present technology, it is possible to improve a clinical test or treatment in various aspects such as quality and cost. It should be noted that the effects described herein are not necessarily limited, and any of the effects described herein may be produced.

BRIEF DESCRIPTION OF DRAWINGS

FIG. 1 is a diagram showing a state where a clinical test of a certain disease is performed by a certain test method.

FIG. 5 is a diagram showing an example of fields (items) in each record that configures a database 47a.

Figure 2:
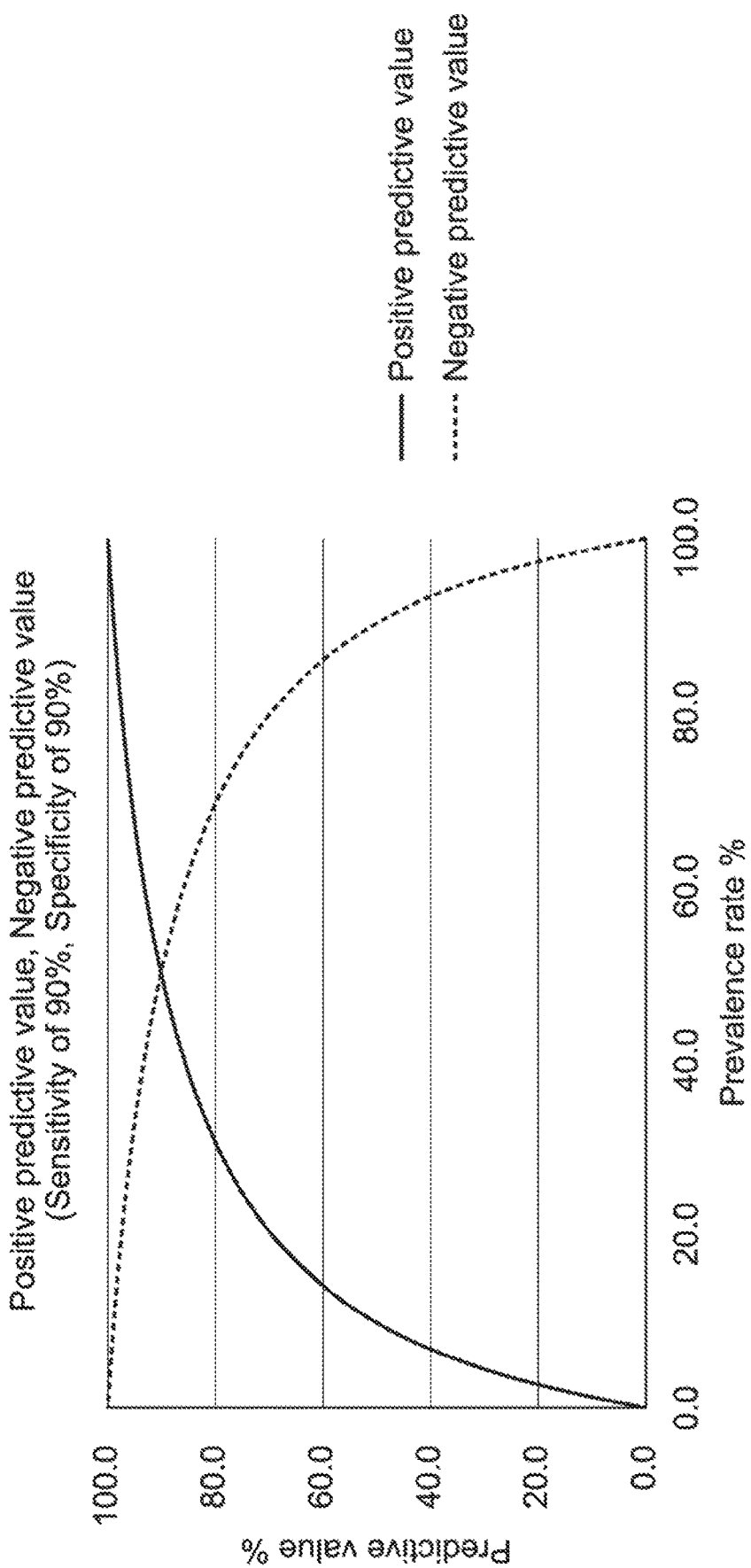
FIG. 2 is a graph showing a relationship between a positive predictive value and a negative predictive value, and a prevalence rate.

Hereinafter, embodiments of the present technology will be described with reference to the drawings.

REGARDING BACKGROUND

In test devices, test agents, and test kits (hereinafter, correctively referred to as test device) used in clinical practice, the degree of sensitivity and the degree of specificity are defined. With the degree of sensitivity, the test device can correctly determine an affected patient to be positive. With the degree of specificity, the test device can correctly determine an unaffected person to be negative. Those degrees of accuracy can be specified at the time the test device is manufactured. Until now, a final determination of a doctor on a test result has been made with reference to those indices in clinical tests.

In contrast to this, for the positive or negative result shown by the test device, there are indices of a positive predictive value and a negative predictive value that serve as indices representing a probability on whether a patient is actually affected with a disease or not.

The positive predictive value and the negative predictive value are very important indices, which represent a probability of a test result, for a doctor who uses the test device in clinical practice to determine a diagnosis of a disease. The reason why it is important will be described later. The positive predictive value and the negative predictive value can be calculated from the sensitivity and the specificity of the test device, and a prevalence rate. Conversely, in the case where the prevalence rate varies from hour to hour in infectious diseases and the like, the values of those indices also vary from hour to hour.

In the present technology, the prevalence rate, which varies from hour to hour, is adequately handled to assist a doctor to determine a more definite diagnosis using a test terminal in pandemic of an infectious disease, for example. This is one object to develop this test system.

In other words, examples in which information related to infection is provided by public institutions are already found, but it has been difficult to immediately provide detailed information to correspond to each test device or each patient. Immediately providing detailed information in such a manner is also one object to develop this test system.

[Regarding Data Items Necessary for Calculating Sensitivity and Specificity]

Here, data items necessary for calculating a sensitivity and a specificity will be described. FIG. 1 shows a result of a clinical test of a certain disease is performed by a certain test method.

Here, true positive "a" is the number of persons who apply to a case in which a positive result is obtained by a test device and a doctor makes a final determination for a certainty that the patient is affected with a disease (test positive/diagnosis positive).

False negative "b" is the number of persons who apply to a case in which a negative result is obtained by a test device but a doctor makes a final determination for a certainty that the patient is affected with a disease (test negative/diagnosis positive).

False positive "c" is the number of persons who apply to a case in which a positive result is obtained by a test device but a doctor makes a final determination for a certainty that the patient is not affected with a disease (test positive/diagnosis negative).

True negative "d" is the number of persons who apply to a case in which a negative result is obtained by a test device but a doctor makes a final determination for a certainty that the patient is not affected with a disease (test negative/diagnosis negative).

A prevalence rate, a sensitivity and a specificity are determined using each value of the above-described true positive "a", false negative "b", false positive "c" and true negative "d" as follows:

Prevalence rate=$(a+b)/(a+b+c+d)$

Sensitivity=$a/(a+b)$

Specificity=$d/(c+d)$

In addition, positive, negative, positive rate, negative rate, positive predictive value, negative predictive value, number of diseases, number of non-diseases, total number, and accuracy are determined using each value of the above-described true positive "a", false negative "b", false positive "c" and true negative "d" as follows:

Positive=$a+c$

Negative=$b+d$

Positive rate=$(a+c)/(a+b+c+d)$

Negative rate=$(b+d)/(a+b+c+d)$

Positive predictive value=$a/(a+c)$

Negative predictive value=$d/(b+d)$

Number of diseases=$a+b$

Number of non-diseases=$c+d$

Total number=$a+b+c+d$

Accuracy=$(a+d)/(a+b+c+d)$

It should be noted that in the case where there are a plurality of diseases or test methods, a table like this figure can be created for each combination of the diseases and the test methods.

[Relationship Between Prevalence Rate, and Positive Predictive Value and Negative Predictive Value]

Next, a relationship between the prevalence rate, and the positive predictive value and the negative predictive value will be described.

First, according to Bayes' theorem, a probability (odds) that a patient is subjected to a certain test and determined to be actually affected with a disease is represented as the following mathematical expression (1), using pretest odds in which a positive result is obtained in a test before the test is performed, and a likelihood ratio.

$$\text{posttest odds} = \text{pretest odds} \times \text{likelihood ratio} \quad (1)$$

Further, odds ($\Omega$) are represented by the following mathematical expression (2) using a probability (p).

$$\Omega = p/(1-p) \quad (2)$$

It should be noted that from the mathematical expression (2), the probability (p) is represented by the following mathematical expression (3) using the odds ($\Omega$).

$$p = \Omega/(1+\Omega) \quad (3)$$

Further, posttest positive odds (that will be described later) are represented by the following mathematical expression (4) using the pretest odds and a positive likelihood ratio (that will be described later).

$$\text{posttest positive odds} = \text{pretest odds} \times \text{positive likelihood ratio} \quad (4)$$

Furthermore, posttest negative odds (that will be described later) are represented by the following mathematical expression (5) using the pretest odds and a negative likelihood ratio (that will be described later).

$$\text{posttest negative odds} = \text{pretest odds} \times \text{negative likelihood ratio} \quad (5)$$

Here, the definition expressions of relationships among other indices are also represented by the following mathematical expressions (6) to (11).

$$\text{prevalence rate} = \text{number of diseases/total number} \quad (6)$$

$$\text{pretest odds} = \text{prevalence rate}/(1-\text{prevalence rate}) \quad (7)$$

$$\text{posttest positive odds} = \text{positive predictive value}/(1-\text{positive predictive value}) \quad (8)$$

$$\text{posttest negative odds} = \text{negative predictive value}/(1-\text{negative predictive value}) \quad (9)$$

$$\begin{aligned}\text{positive likelihood ratio} &= \text{sensitivity}/(1-\text{specificity}) \\ &= (\text{number of true positive/number of diseases})/ \\ &\quad (\text{number of false positive/number of non-diseases})\end{aligned} \quad (10)$$

$$\begin{aligned}\text{negative likelihood ratio} &= (1-\text{sensitivity})/\text{specificity} \\ &= (\text{number of false negative/number of diseases})/ \\ &\quad (\text{number of true negative/number of non-diseases})\end{aligned} \quad (11)$$

By the above mathematical expressions, the positive predictive value and the negative predictive value are represented by the following mathematical expressions (12) and (13) using the prevalence rate, the sensitivity, and the specificity.

$$\text{positive predictive value} = \text{sensitivity} \times \text{prevalence rate}/(\text{sensitivity} \times \text{prevalence rate} + (1-\text{prevalence rate})(1-\text{specificity})) \quad (12)$$

$$\text{negative predictive value} = \text{specificity} \times (1-\text{prevalence rate})/(\text{specificity} \times (1-\text{prevalence rate}) + \text{prevalence rate} \times (1-\text{sensitivity})) \quad (13)$$

It should be noted that the mathematical expressions described above may be represented using the probability (p) or using the odds ($\Omega$), and information to be obtained are synonymous.

Next, the relationship between the positive predictive value and the negative predictive value, and the prevalence rate will be described in more details. FIG. 2 is a graph showing a relationship between the positive predictive value and the negative predictive value, and the prevalence rate. It should be noted that in a test device to be used in this test, a sensitivity is 90%, and a specificity is 90%.

From the graph, for example, when the prevalence rate is 50%, that is, when the number of patients who are actually affected with a disease is approximately half the number of patients who are subjected to diagnoses, the positive predictive value and the negative predictive value are each approximately 90%, and it is found that a test result can be trusted.

However, for example, when the prevalence rate is approximately 5%, that is, when 100 persons are subjected to diagnoses and there are approximately 5 persons affected with a disease, the positive predictive value is approximately 30%, and it is found that a test result is difficult to trust.

Though not shown in this graph, for example, even in the case of using a test device having a sensitivity of 99% in order to increase the degree of accuracy of diagnosis, if the prevalence rate is extremely low, the positive predictive value falls below 50% and the reliability of the test result is reduced.

[Regarding Presentation of Treatment Plan Based on Positive Predictive Value and Negative Predictive Value]

Next, description will be given on a configuration to specify a treatment plan based on the positive predictive value and the negative predictive value by the test server, and to transmit and present a result to the test terminal.

(Regarding Important Index in MRSA Infection)

Here, infection of MRSA (Methicillin-resistant *Staphylococcus aureus*) will be exemplified.

In order to prevent nosocomial infection, it is necessary to individually manage MRSA-infected patients. In the individual management, expense for infection prevention measures such as expense for a private room, and burdens of healthcare professionals, such as hand-washing and wearing of aprons, are required.

In order to reduce those burdens as much as possible, it is important to make a correct diagnosis on whether such a patient is really affected with MRSA or not. Examples of the test method include a genetic test, immunoassay, and a cultivation test. If the presence or absence of infection of MRSA is tested by those tests and a MRSA-uninfected person can be correctly diagnosed to be MRSA negative, the number of affected persons to be individually managed can be reduced, and the expense for infection prevention measures can be reduced. From this viewpoint, the negative predictive value is important regarding MRSA infection.

(Regarding Example of Plan Presented in MRSA Infection)

Next, a specific example will be given regarding a plan to be adopted depending on the levels of the prevalence rate, the sensitivity, the specificity, and the negative predictive value.

For example, when a test method in which the sensitivity is 85% and the specificity is 90% is used, if the prevalence rate is 40% or less, the negative predictive value of this test is 90% or more. The test server thus presents a recommendation for implementation of the test.

If the prevalence rate is more than 40%, the negative predictive value of this test is less than 90%. The test server thus does not recommend this test, and presents a recommendation for implementation of another test method with a higher sensitivity or a recommendation for implementation of individual management of patients without performing a test.

Similarly, when a test method in which the sensitivity is 90% and the specificity is 90% is used, if the prevalence rate is 50% or less, the negative predictive value is 90% or more. The implementation of the test is thus recommended. If the prevalence rate is above 50%, the negative predictive value is less than 90%. The test server thus does not recommend implementation of this test, and presents a recommendation for implementation of another test method with a higher sensitivity or a recommendation for implementation of individual management of patients.

Similarly, when a test method in which the sensitivity is 95% and the specificity is 90% is used and when the prevalence rate is 66.7% or less, the negative predictive value is 90% or more. The implementation of the test is thus recommended. If the prevalence rate is more than 66.7%, the negative predictive value is less than 90%. The test server thus does not recommend the test, and recommends another test method with a higher sensitivity or recommends individual management of patients.

(Regarding Recommendation of Test Method Based on Prevalence Rate)

Next, description will be given on what test method can be recommended to a doctor by the test server based on the prevalence rate.

As described above, there is a predetermined relationship among the sensitivity, the specificity, the prevalence rate, and the negative predictive value. In this regard, in the case where the negative predictive value is intended to be 90% or more when the prevalence rate is 30%, it is found that a test method with the sensitivity of 77% and the specificity of 90% or more only needs to be used.

Further, in the case where the negative predictive value is intended to be 90% or more when the prevalence rate is 40%, it is found that a test method with the sensitivity of 85% and the specificity of 90% or more only needs to be used.

Furthermore, in the case where the negative predictive value is intended to be 90% or more when the prevalence rate is 50%, it is found that a test method with the sensitivity of 90% and the specificity of 90% or more only needs to be used.

Moreover, in the case where the negative predictive value is intended to be 90% or more when the prevalence rate is 60%, it is found that a test method with the sensitivity of 93% and the specificity of 90% or more only needs to be used.

When this is applied to a specific case example, for example, the test terminal recommends a test method to be executed to a doctor as follows. Specifically, when the prevalence rate is 30%, use of an immunochromatographic test kit is recommended. The immunochromatographic test kit provides a low sensitivity but can suppress costs. When the prevalence rate is 50%, it is conceived that a genetic test kit that is expensive but provides a high sensitivity or a cultivation test that takes a long test time but provides a high sensitivity is recommended.

It should be noted that in the test system, a list of test methods that are feasible in healthcare facilities in which tests are performed may be held, and an optimum test method may be recommended to a doctor based on the sensitivity, the specificity, the prevalence rate, and the negative predictive value.

[Regarding Specific Example of Prevalence Rate]

Next, a specific example of the prevalence rate described above will be described. Here, an example will be described in which the prevalence rate changes depending on age ranges, regions, periods, ages, communities, and the like.

(Example in which Prevalence Rate Changes Depending on Age Range)

First, description will be given on a state where the prevalence rate of drug-resistant bacteria changes with the lapse of the age range. Description here is based on information on a morbidity change in drug-resistant bacteria, which is created by CDC (Centers for Disease Control and Prevention) of the United States of America. It should be noted that the morbidity and the prevalence rate are similar indices. Here, the morbidity is replaced with the prevalence rate for description.

In the United States of America, the proportion of Methicillin-resistant *Staphylococcus aureus* (MRSA) to *Staphylococcus aureus* is approximately 5% in 1980, whereas the proportion changes to approximately 30% in 1990 and approximately 50% in 2000. Similarly, the proportion of Vancomycin-resistant *Enterococcus* (VRE) to enterococci or the proportion of Fluoroquinolone-resistant *Pseudomonas aeruginosa* (FQRP) to pneumococci is 2% or less in 1990, whereas the proportion changes to 20% or more in 2000.

As described above, since the prevalence rate of drug-resistant bacteria changes with lapse of the age range, in order to enhance the degree of accuracy of a diagnosis, it is important to grasp the latest prevalence rate when a test is performed.

(Example in which Prevalence Rate Changes Depending on Regions (Countries))

Next, description will be given on a state where the prevalence rate of drug-resistant bacteria changes depending on regions (countries). Description here is based on materials of Euro Surveillance 2008 Nov. 20 Volume 13, Issue 47 by European Antimicrobial Resistance Surveillance System (EARSS). The materials show prevalence rates of drug-resistant bacteria on a country-by-country basis in Europe.

According to the materials of EARSS, the proportion of VRE to enterococci in 2007 is 30% or more in Ireland and Greece, 30 to 20% in the United Kingdom, 20 to 10% in Czech Republic, 10 to 5% in Italy, Germany, and Portugal, 5 to 1% in Spain, France, Switzerland, Austria, and other countries, and 1% or less in Norway, Sweden, Finland, Pohland, and other countries.

As described above, since the prevalence rate also differs depending on regions and countries, in order to enhance the degree of accuracy of a diagnosis, it is important to grasp the latest prevalence rate of a region where a test is performed.

(Example 1 of Prevalence Rate of Influenza Virus)

Next, description will be given on a state where the prevalence rate of influenza virus fluctuates depending on periods and regions. Here, materials of Tokyo Metropolitan Institute of Public Health are used. The materials show the number of patients affected with influenza per sentinel on a period basis and on a yearly basis.

According to the materials, the prevalence rate of influenza virus tends to be low in June and July, whereas it tends to be high in February and March every year. However, in such a tendency, an epidemic start period differs yearly, and its prevalence rate also largely differs. Further, as in the epidemic of pandemic strains (H1pdm) in 2009, the prevalence rate is sometimes increased in October, November, and December in which the epidemic does not occur in usual years.

Further, though not shown in the figures here, also in Infectious Agents Surveillance Report (IASR, http://idsc.nih.go.jp/iasr/influ.html) of National Institute of Infectious Diseases, the number of cases of infection of pathogens in sentinels and other healthcare facilities, health departments, and the like is reported as a report of infectious disease surveillance from prefectural and municipal public health institutes. According to the IASR, it is found that there is a difference in period and region of influenza epidemic. Additionally, there is a difference in period and region of influenza epidemic depending on types of influenza viruses.

As described above, the prevalence rate of the influenza virus largely differs depending on years, periods, and types of viruses. Therefore, in order to enhance the degree of accuracy of a diagnosis, a test system that can collect prevalence rate information very quickly and continuously when a test is performed is effective.

(Example 2 of Prevalence Rate of Influenza Virus)

Next, description will be given on a state where the prevalence rate of influenza virus fluctuates depending on ages of patients or communities to which patients belong. Here, materials of the Ministry of Health, Labour and Welfare and the Koriyama health department of Nara Prefecture are used. The materials show the number of estimated consultations of persons on an age group basis in the infectious disease surveillance of the Ministry of Health, Labour and Welfare.

According to the materials, the prevalence rate of influenza virus in the ages of 0 to 14, particularly in the ages of 5 to 9 tends to be higher than the other age groups. In other words, the prevalence rate largely changes depending on the age group.

As a result, it is important to determine a test result using an optimum prevalence rate according to the age of a subject being tested.

Further, the prevalence rate also differs depending on communities to which patients belong. For example, the "Status of Pandemic Influenza in the season of 2012 to 2013", which is reported by the Koriyama health department of Nara Prefecture, provides a report example in which the prevalence rate of influenza virus in early elementary school years is high. For example, there is provided a report example in which the prevalence rate in the first year grade of a certain elementary school in the season of 2011 to 2012 is 30% or more.

On the other hand, according to the hospital admission surveillance and the infectious disease surveillance of the Ministry of Health, Labour and Welfare, the prevalence rate of influenza-like virus in the season of 2011 to 2012 in Japan is estimated as 16,480,000 persons. Assuming that the population of Japan is 128 million persons based on the result of the census in 2010, the prevalence rate of influenza virus is 12.9% at a maximum, which differs from the example of Nara Prefecture. In other words, this suggests that the prevalence rate of influenza virus differs depending on communities.

As a result, it is important to determine a test result using an optimum prevalence rate according to communities to which subjects being tested belong.

Hereinbefore, the specific example of the prevalence rate has been described.

[Regarding Configuration of Test System]

Figure 3:
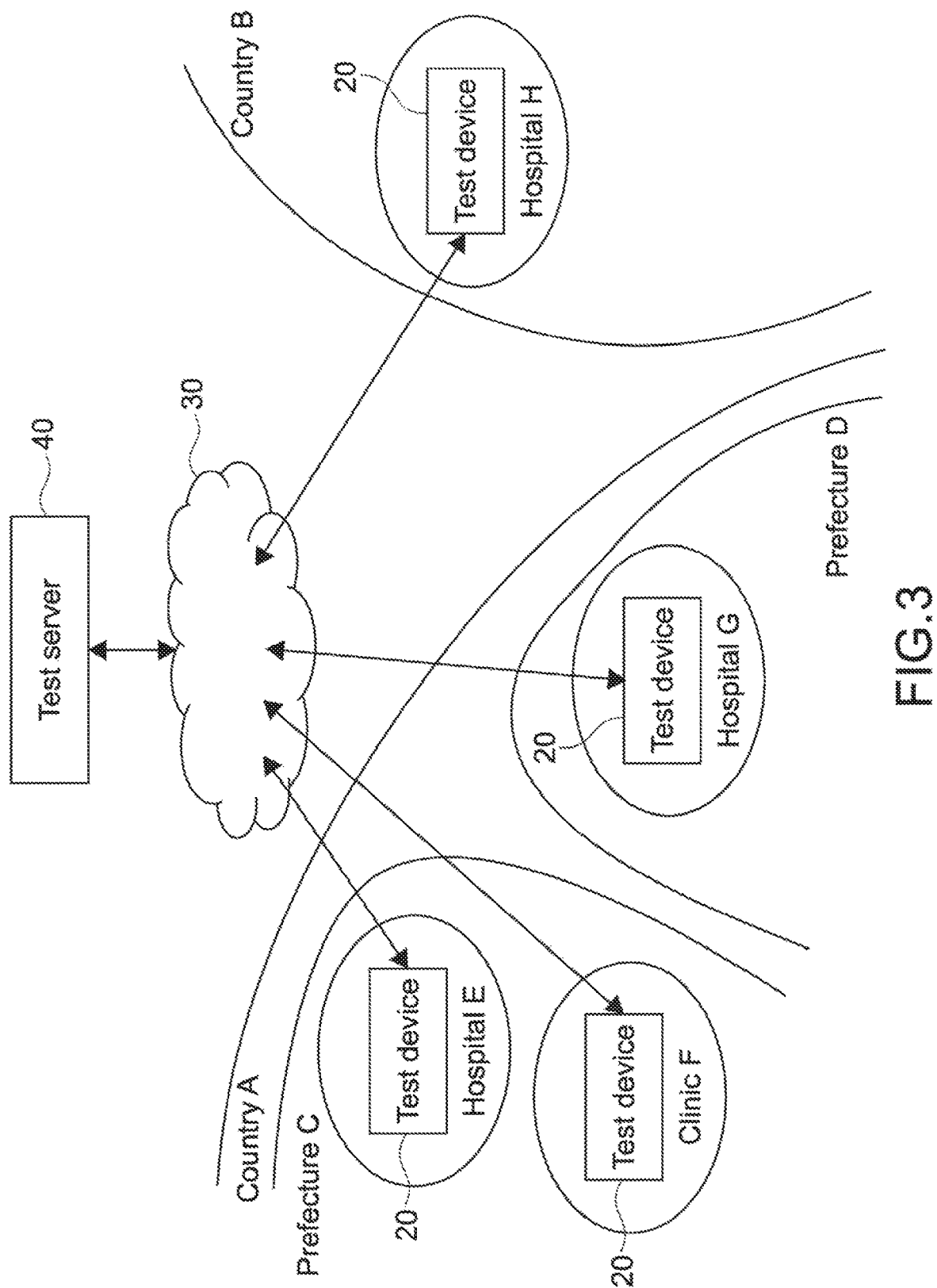
FIG. 3 is a diagram showing a configuration in which a test system 10 that adopts the present technology connects test terminals 20 with a test server 40 via a network.

Next, the overall configuration of a test system to which the present technology is applied will be described. In a test system using the present technology, a client server configuration is adopted. FIG. 3 is a diagram showing a configuration in which a test system 10 that adopts the present technology connects test terminals 20 with a test server 40 via a network. As shown in this figure, in the test system 10 that adopts the present technology, a plurality of test terminals 20 serving as clients are dispersedly disposed in countries, regions, and facilities and are connected to the test server 40 via the network 30.

(Reason why Client Server Configuration is Adopted)

First, the reason why the test system 10 that adopts the present technology has to have a client server configuration will be described.

As described above, using the latest prevalence rate is one of points in the present technology. As found from the definition described above, regarding this prevalence rate, as the total number of tests becomes larger, the degree of accuracy of a calculated prevalence rate becomes higher.

Further, in order to increase the total number of tests, there are an approach to performing many tests in one test terminal and an approach to collecting test results from many test terminals. In the present technology, in order to achieve an approach to collecting test results from many test terminals, a client server configuration formed of the test server 40 and the plurality of test terminals 20 is adopted as a configuration of the test system 10.

Adopting this configuration allows the number of test terminals 20 serving as clients to be increased as much as possible. This can improve the degree of accuracy of the prevalence rate provided from the test server 40 to the test terminals 20.

(Regarding Configuration of Test Server 40)

Figure 4:
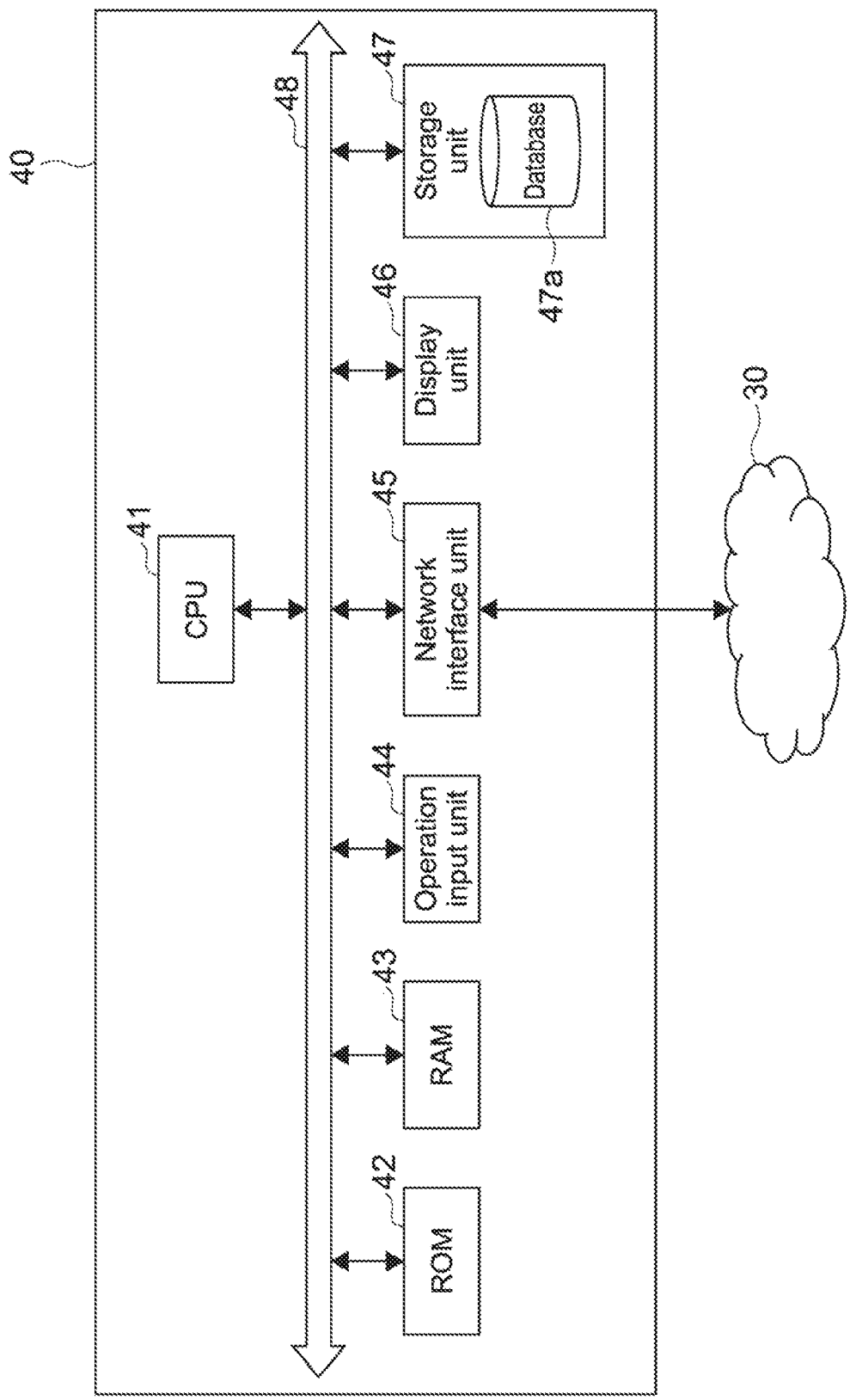
FIG. 4 is a block diagram of a case where the test server 40 is configured by a general computer.

Next, a hardware configuration of the test server 40 will be described. The test server 40 may be configured by dedicated hardware or software or may be configured by a general computer. FIG. 4 is a block diagram of a case where the test server 40 is configured by a general computer.

As shown in the figure, the test server 40 includes a CPU (Central Processing Unit, control unit, first control unit) 41, a ROM (Read Only Memory) 42, a RAM (Random Access Memory) 43, an operation input unit 44, a network interface unit (communication unit, first communication unit) 45, a display unit 46, and a storage unit 47, and those blocks are connected to one another via a bus 48.

The ROM 42 fixedly stores a plurality of programs and data such as firmware to execute various types of processing. The RAM 43 is used as a work area of the CPU 41 and temporarily holds an OS (Operating System), various applications being executed, and various types of data being processed.

The storage unit 47 is, for example, an HDD (Hard Disk Drive), a flash memory, or another non-volatile memory such as a solid-state memory. In the storage unit 47, a database 47a that will be described later is stored in addition to the OS, the various applications, and the various types of data.

The network interface unit 45 is connected to the network 30 for exchanging information with the test terminals 20, and collects information from the test terminals 20 or provides processed information to the test terminals 20.

The CPU 41 develops a program corresponding to a command provided from the operation input unit 44, in a plurality of programs stored in the ROM 42 and the storage unit 47, to the RAM 43 and appropriately controls the display unit 46 and the storage unit 47 according to the developed program.

Further, the CPU 41 updates the database 47a based on information collected from the test terminals 20 via the network 30 and the network interface unit 45. The CPU 41 then extracts necessary information from the database 47a based on a condition designated by a demand of the information received from the test terminals 20, counts and returns the information to the test terminals 20.

The operation input unit 44 is, for example, a pointing device such as a mouse, a keyboard, a touch panel, or another operating device.

The display unit 46 is, for example, a liquid crystal display, an EL (Electro-Luminescence) display, a plasma display, or a CRT (Cathode Ray Tube) display. The display unit 46 may be incorporated in the test server 40 or may be externally connected.

Hereinbefore, the configuration of the test server 40 has been described.

(Regarding Database 47a)

Next, a configuration example of records stored in the database 47a will be described. FIG. 5 is a diagram showing an example of fields (items) in each record that configures the database 47a. It should be noted that those items are referred to as test information items.

The test information items are configured of a plurality of information items such as instrument ID, patient ID, sample ID, date of test, address, country, gender, age, test result, diagnosis result of doctor, disease ID, test method ID, and elapsed time from the development of a disease.

(Regarding Configuration of Test Terminal 20)

Figure 6:
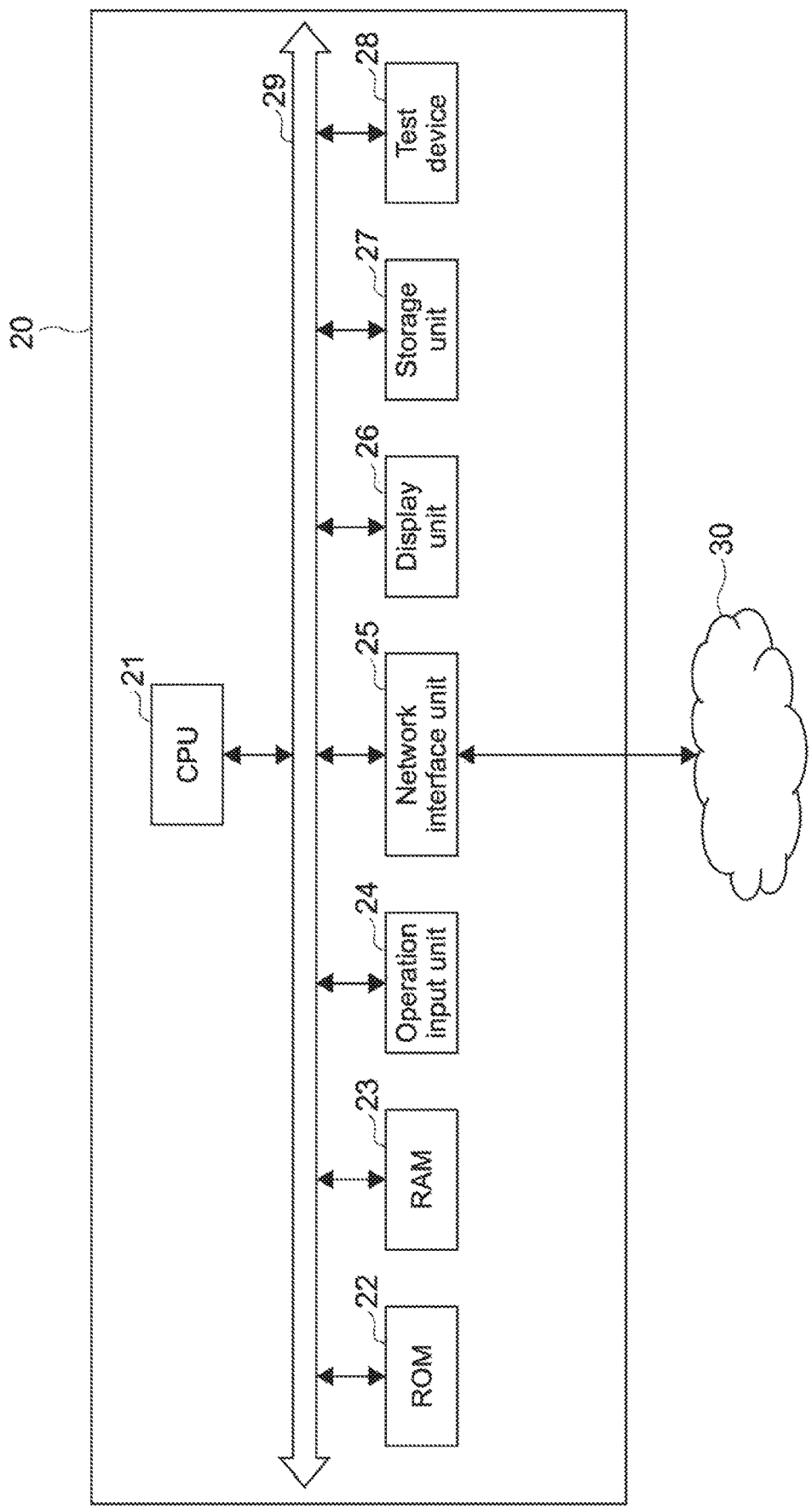
FIG. 6 is a block diagram of a case where the test terminal 20 is configured by a test device and a general computer.

Next, a hardware configuration of the test terminal 20 will be described. The test terminal 20 may be configured by dedicated hardware or software or may be configured by a test device and a general computer. FIG. 6 is a block diagram of a case where the test terminal 20 is configured by a test device and a general computer.

As shown in the figure, the test terminal (communication terminal) 20 includes a CPU (control unit, second control unit) 21, a ROM 22, a RAM 23, an operation input unit (input unit) 24, a network interface unit (communication unit, second communication unit) 25, a display unit 26, a storage unit 27, and a test device 28, and those blocks are connected to one another via a bus 29. It should be noted that description of constituent elements having the same functions as those of the test server 40 will be omitted.

The network interface unit 25 is connected to the network 30 for exchanging information with the test server 40, and transmits information to the test server 40 or receives information processed in the test server 40.

The CPU 21 presents information, which is received from the test server 40 via the network 30 and the network interface unit 25, to a user or a doctor via the display unit 26, or performs various types of processing based on the received information. The various types of processing will be described later. Further, the CPU 21 transmits a test result in the test device 28 or a final diagnosis of a doctor who made a diagnosis of a disease to the test server 40 via the network 30 and the network interface unit 25.

The test device 28 is a device with which a disease is actually tested. A test result is read by the CPU 41, and then presented to a doctor who performed the test via the display unit 26 or transmitted to the test server 40 via the network 30. It should be noted that in the case where a test kit is used as the test device, the test terminal 20 may automatically read a test result, or a test result may be input to the test terminal 20 manually.

[Regarding Processing Flow of Test System 10]

Next, an operation of the test system 10 will be described.

In the test system, the test information items are transmitted from one or more test terminals 20 to the test server 40. The test information items transmitted from the test terminals 20 to the test server 40 are accumulated as needed in a database 47a. The test server 40 starts tabulation procession of the test information items in a constant time period, for example.

The test server 40 performs tabulation processing about test information items depending on predesignated conditions. As a result of the tabulation processing, values of the prevalence rate, the sensitivity, and the specificity are determined depending on the conditions. Here, the conditions include a type of a test method (test method ID), elapsed time from the development of a disease, gender, age, place, group or a combination thereof. The tabulation processing of the test information items is performed by using each value of the above-described true positive "a", false negative "b", false positive "c" and true negative "d".

Hereinafter, a detailed operation of the test system 10 will be described.

(1. Overall Operation of Test System 10)

Figure 7:
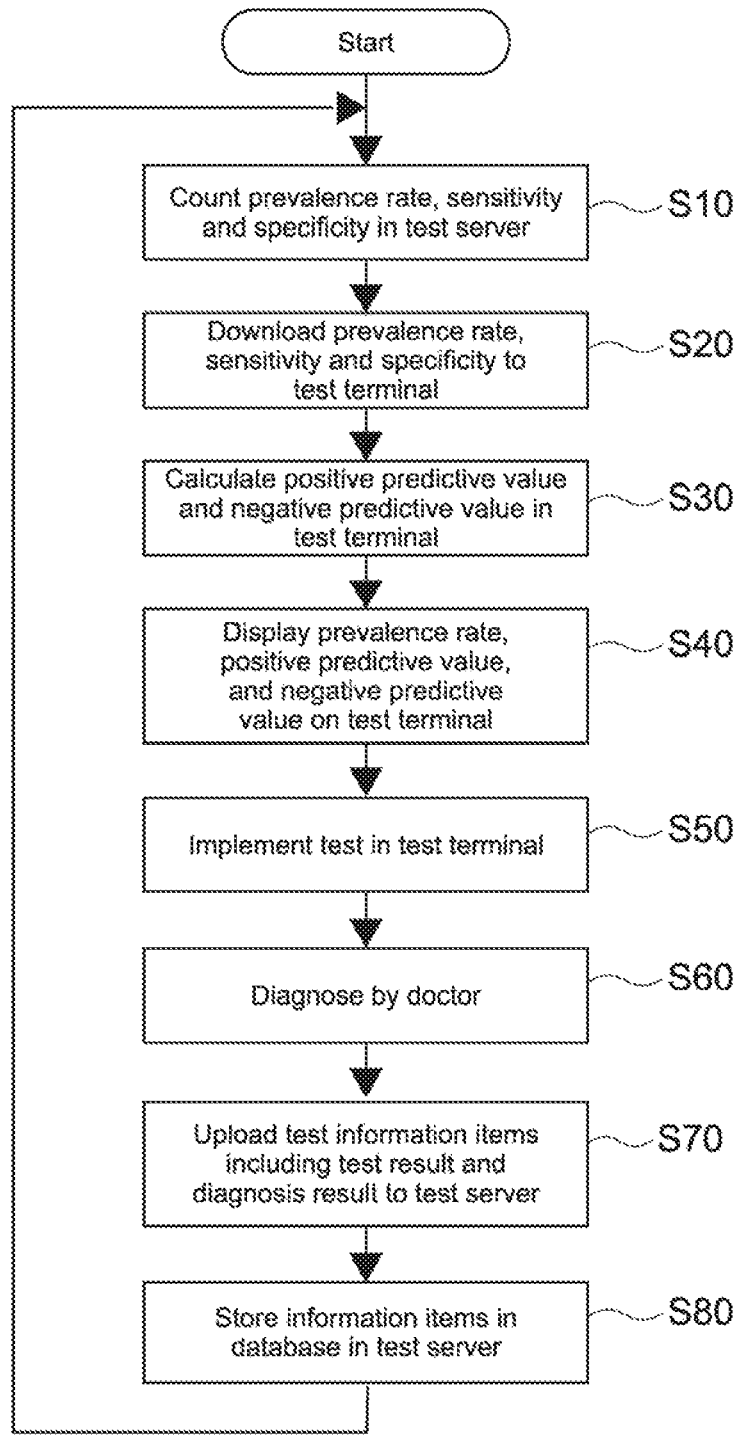
FIG. 7 is a flowchart showing overall processing flow in the test system 10.

FIG. 7 is a flowchart a flowchart showing overall processing flow in the test system 10.

A plurality of test information items collected from one or more test terminals 20 are already accumulated in the database 47a in the test server 40.

The CPU 41 of the test server 40 extracts the test information items from the database 47a based on predesignated conditions. The conditions are those that a test method ID, elapsed time from the development of a disease, etc. are designated.

The CPU 41 of the test server 40 counts and calculates a prevalence rate for one disease, a sensitivity and a specificity based on the test information items extracted from the database 47a (Step S10). It should be noted that the count and calculation processing may be started on a certain-time-period basis (for example, every hour or every day) or may be started at a timing designated by a human.

The CPU 21 of the test terminal 20 downloads the information items about the latest prevalence rate, the sensitivity and the specificity from the test server 40 (Step S20). It should be noted that downloading may be performed by pull communication from the test terminal 20 or by push communication from the test server 40.

The CPU 21 of the test terminal 20 calculates a positive predictive value and a negative predictive value according to the mathematical expressions (12) and (13) described above (Step S30).

The CPU 21 of the test terminal 20 presents the prevalence rate, the positive predictive value, and the negative predictive value calculated to a user, i.e., a doctor, via the display unit 26 (Step S40).

Next, the user (doctor) at the test terminal 20 implements a test to a patient's case using the test device 28 (Step S50). The test result by the test device 28 is automatically input to the test terminal 20, for example, input manually by the doctor. The test result is displayed on the display unit 26.

Furthermore, the doctor determines a diagnosis about the case on which the test is performed by referring to the prevalence rate, the positive predictive value, the negative predictive value. The diagnosis result of the doctor is input manually to the test terminal 20 (Step S60). It should be noted that the diagnosis result at least includes the information items such as disease ID, test method ID, positive/negative and elapsed time from the development of a disease.

Thereafter, the CPU 21 of the test terminal 20 generates the test information items including patient information input by the doctor in advance, the test result and the diagnosis result, and transmits them to the input server 40 (Step S70).

The patient information includes various types of attribute information concerning to the patient such as Patient ID, Address (address, administrative district), Country, Gender, Age, and Belongs (organization, company, other group). The patient information is input and registered to the test terminal 20 in advance by the doctor, or the like.

The CPU 41 of the test server 40 registers the test information transmitted from the test terminal 20 to the database 47*a* (Step S80). Thereafter, the processing returns to Step S10, and the above-described processing is repeated.

(2. Calculation Processing of Prevalence Rate by Test Server 40)

Figure 8:
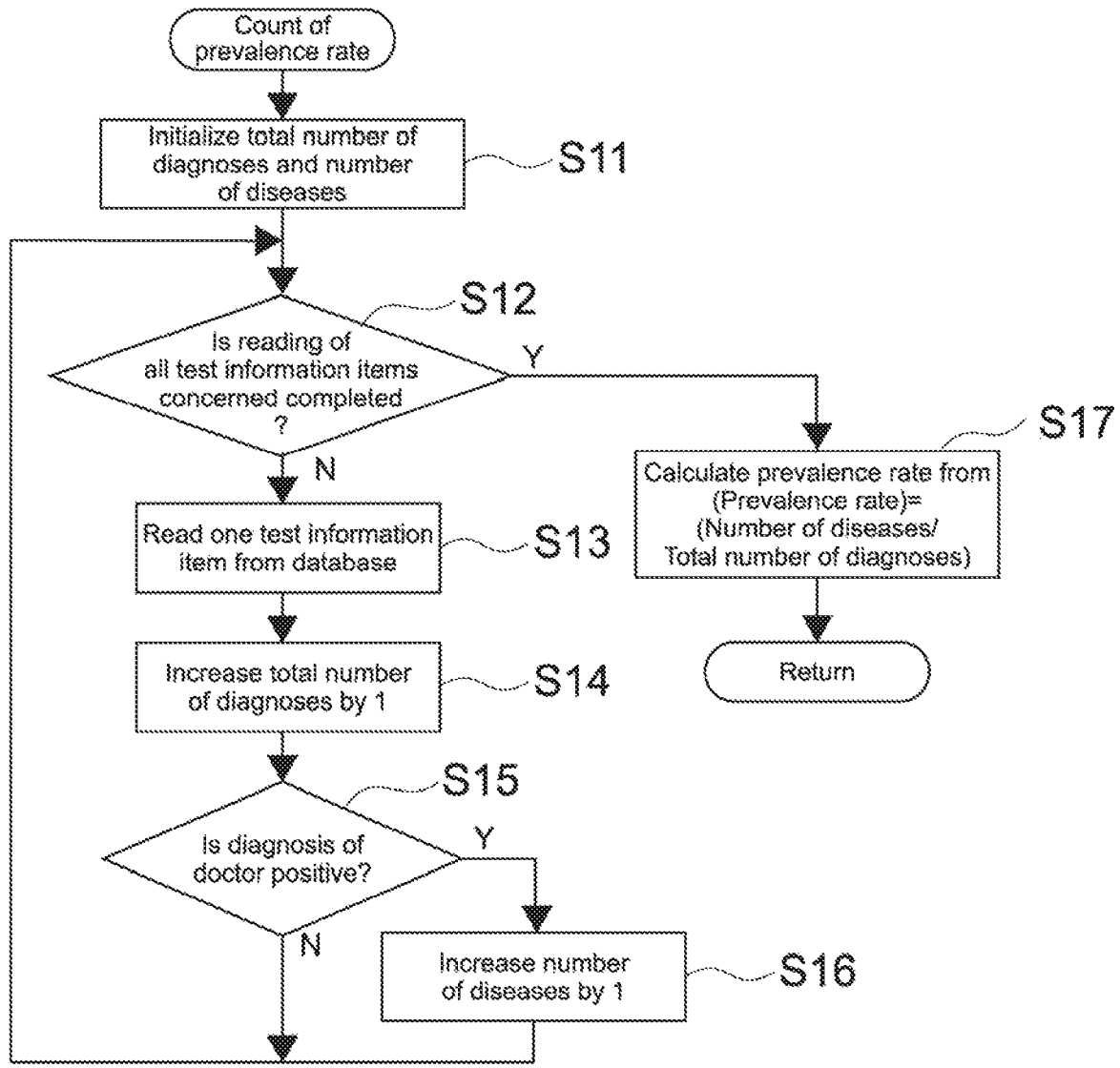
FIG. 8 is a flowchart for describing the details of processing to count and calculate a prevalence rate.

Next, referring to FIG. 8, the calculation processing of the prevalence rate by the test server 40 will be described.

First, the CPU 41 of the test server 40 clears the total number of diagnoses and the number of diseases to zero for initialization that are variables used for count up at the time of count (Step S11).

Next, the CPU 41 of the test server 40 determines whether all test information items that satisfy the conditions of the test information items to be processed stored in the database 47*a* are read or not (Step S12). Here, the conditions of the test information items to be processed include, for example, a specific test method ID.

When the test information items that satisfy the conditions of the test information items to be processed remain on the database 47*a* (N of Step S12), the CPU 41 of the test server 40 reads one test information item (Step S13), and counts up the total number of diagnoses by 1 (Step S14).

Next, the CPU 41 of the test server 40 determines whether the diagnosis result within the test information items read is positive or not (Step S15). When the result is positive (Y of Step S15), the CPU 41 counts up the number of diseases by 1 (Step S16).

When the diagnosis result within the test information items read from the database 47*a* is negative (N of Step S15) and next test information item that satisfies the test information items to be processed is present at the database 47*a* (Y of Step SA12), the test information item is read, and the operations from Step S13 to Step 15 or Step S16 are repeated.

In Step S12, when there are no test information items stored in the database 47*a* that satisfy the conditions of the test information items to be processed (Y of Step S12), the CPU 41 calculates a prevalence rate from the total number of diagnoses and the number of diseases according to the mathematical expression (6) (Step S17). It should be noted that the mathematical expression (6) is as follows.

$$\text{prevalence rate} = \text{number of diseases/total number} \quad (6)$$

In the above description, the prevalence rate is determined from the test server 40, but a value of the prevalence rate may be acquired from outside the test system 10. A method of acquiring the value of the prevalence rate from outside may be a method passing through the network 30 or may be a method of extracting a numerical value of the prevalence rate from a research paper and the like and manually inputting the numerical value. When a numerical value from a research paper and the like is manually input to the test server 40, it is desirable to have a standard to simplify the input.

The CPU 41 of the test server 40 may transmit the prevalence rate to the test terminal 20 every time the prevalence rate is calculated.

Alternatively, the CPU 41 of the test server 40 may hold the value of the prevalence rate calculated, and cause the value of the prevalence rate to be responded to the test terminal 20 upon a request from the test terminal 20.

(3. Calculation Processing of Sensitivity and Specificity by Test Server 40 (Part 1))

For example, in the case of a respiratory tract infection disease, it is known that the number of pathogens in the nasal cavity or pharynx fluctuates with the elapsed time from the development of a disease. Along with the change in the number of pathogens, the sensitivity and the specificity of a test also fluctuate. As a result, based on the elapsed time from the development of a disease of a patient, the degree of accuracy of the positive predictive value and negative predictive value to be obtained can be improved using adequate values of the sensitivity and the specificity.

Next, operations of calculating the sensitivity and the specificity by the test server 40 will be described.

The calculation of the sensitivity and the specificity by the test server 40 is performed asynchronously with the calculation of the prevalence rate described above.

Figure 9:
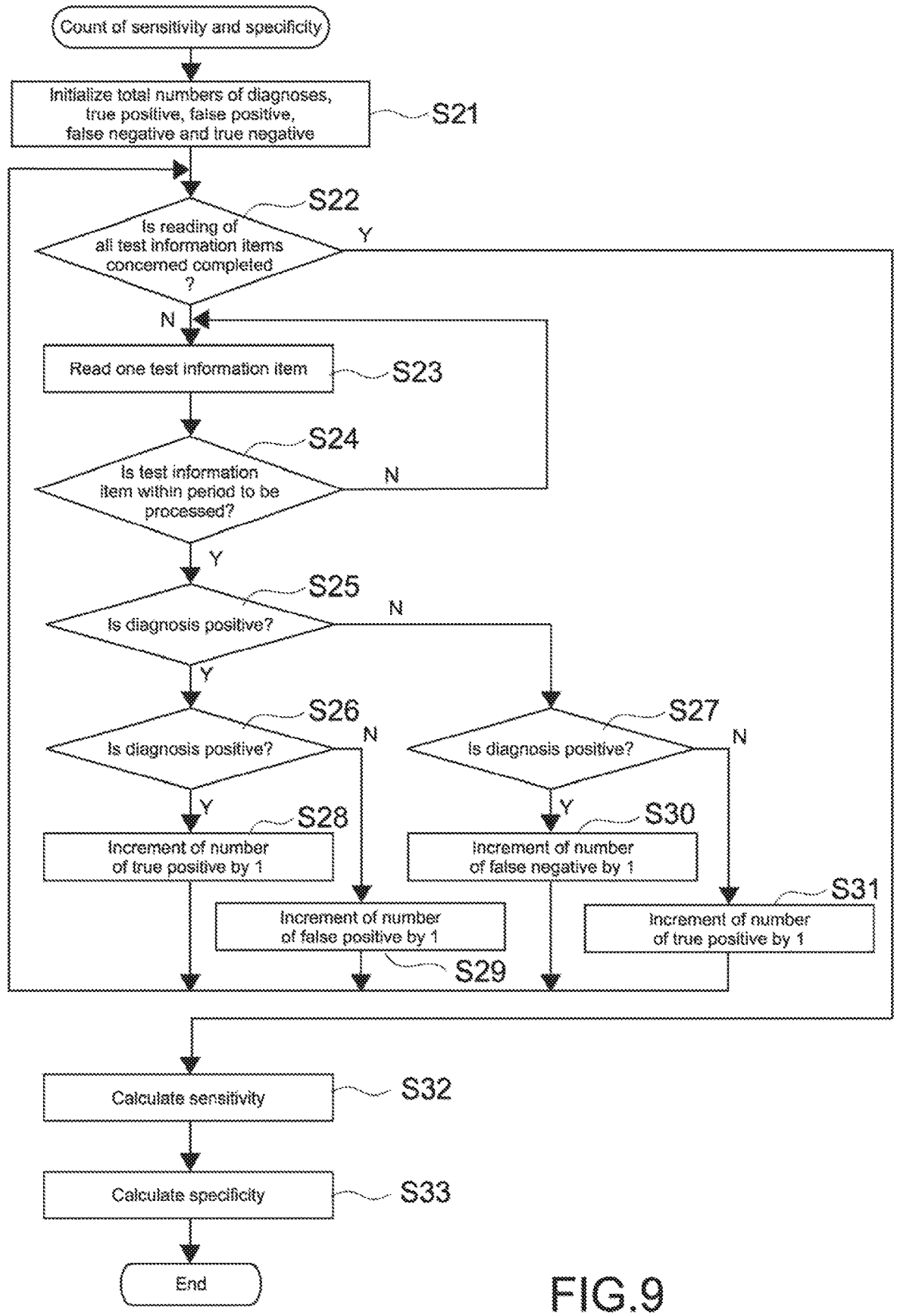
FIG. 9 is a flowchart showing calculation processing (Part 1) of a sensitivity and a specificity by a test server.

FIG. 9 is a flowchart showing calculation processing (Part 1) of a sensitivity and a specificity by the test server 40.

Here, as the condition of the test information items to be processed, the test method ID is determined in advance.

First, the CPU 41 of the test server 40 initializes respective variables used for calculation of the sensitivity and the specificity (Step S21). The variables used for calculation of the sensitivity and the specificity include the number of test positive/diagnosis negative (true positive), the number of test positive/diagnosis negative (false positive), the number of test negative/diagnosis positive (false negative) and the number of test negative/diagnosis negative (true negative).

Next, the CPU 41 determines whether or not all test information items that satisfy the conditions of the test information items to be processed determined in advance in the database 47*a* are read or not (Step S22).

When the test information items that satisfy the conditions of the test information items to be processed remain on the database 47*a* (N of Step S22), the CPU 41 reads one test information item (Step S23).

Next, the CPU 41 determines whether or not elapsed time from the development of a disease included in the test information items read is within a predetermined number of days (Step S24). Here, the predetermined number of days is, for example, one week depending on the types of the diseases to be tested.

In the case where elapsed time from the development of a disease is not within a predetermined number of days (N of Step S24), the CPU 41 reads next test information item from the database 47*a*, and performs again the processing in Step S24 for the test information item.

In the case where elapsed time from the development of a disease is within a predetermined number of days (Y of Step S24), the CPU 41 takes out the respective information items of the test result and the diagnosis result included in the test information items, and updates the above-described respective variables used for calculation of the sensitivity and the specificity based on a combination of the information items (Step S25-Step 31).

Here, the combinations of the test result and the diagnosis result include:

the test result is positive and the diagnosis result is positive (test positive/diagnosis negative: true positive), the test result is positive and the diagnosis result is negative (test positive/diagnosis negative: false positive), the test result is negative and the diagnosis result is positive (test negative/diagnosis positive: false negative), and the test result is negative and the diagnosis result is negative (test negative/diagnosis negative: true negative).

The CPU increments any one of the respective variables of the number of test positive/diagnosis negative (true positive), the number of test positive/diagnosis negative (false positive), the number of test negative/diagnosis positive (false negative) and the number of test negative/diagnosis negative (true negative) for one test information item acquired based on the above-described combination.

Thereafter, the CPU 41 returns to Step S22, and determines whether or not all test information items that satisfy the conditions of the test information items to be processed determined in advance in the database 47*a* are read or not. In the case where all test information items that satisfy the conditions of the test information items to be processed determined in advance in the database 47*a* are read (Y of Step S22), the CPU 41 calculates the sensitivity (Step S32) and the specificity (Step S33).

Here, the sensitivity is calculated by

Sensitivity=number of true positive/(number of true positive+number of false negative)

Here, the specificity is calculated by

Specificity=number of true negative/(number of false true positive+number of true negative)

The processing is started for a certain time period (e.g., hourly, fixed time every day, fixed time every week), for example.

The CPU 41 of the test server 40 may transmit the respective values of the sensitivity and the specificity to the test terminal 20 every time the respective values of the sensitivity and the specificity are calculated.

Alternatively, the CPU 41 of the test server 40 may cause the respective values of the sensitivity and the specificity to be responded to the test terminal 20 upon a request from the test terminal 20.

Though not shown in the flowchart in FIG. 9, the CPU 41 of the test server 40 may calculate the positive predictive value and the negative predictive value based on the prevalence rate, the sensitivity and the specificity. The positive predictive value and the negative predictive value are calculated by the above-described mathematical expressions (12) and (13).

It should be noted that the positive predictive value and the negative predictive value may be determined not using the prevalence rate, the sensitivity and the specificity, but by the number of true positive, the number of false positive, the number of false negative and the number of true negative.

The respective values of the positive predictive value and the negative predictive value calculated may be transmitted to the test terminal 20 every time the respective values calculated.

Alternatively, it may cause the respective values of the sensitivity and the specificity to be responded to the test terminal 20 upon a request from the test terminal 20.

In this manner, in the case where the positive predictive value and the negative predictive value are determined and transmitted to the test terminal 20, the calculation processing (Step S30) of the positive predictive value and the negative predictive value by the test terminal 20 is skipped in a flowchart in FIG. 7.

(4. Calculation Processing of Sensitivity and Specificity by Test Server 40 (Part 2))

Figure 10:
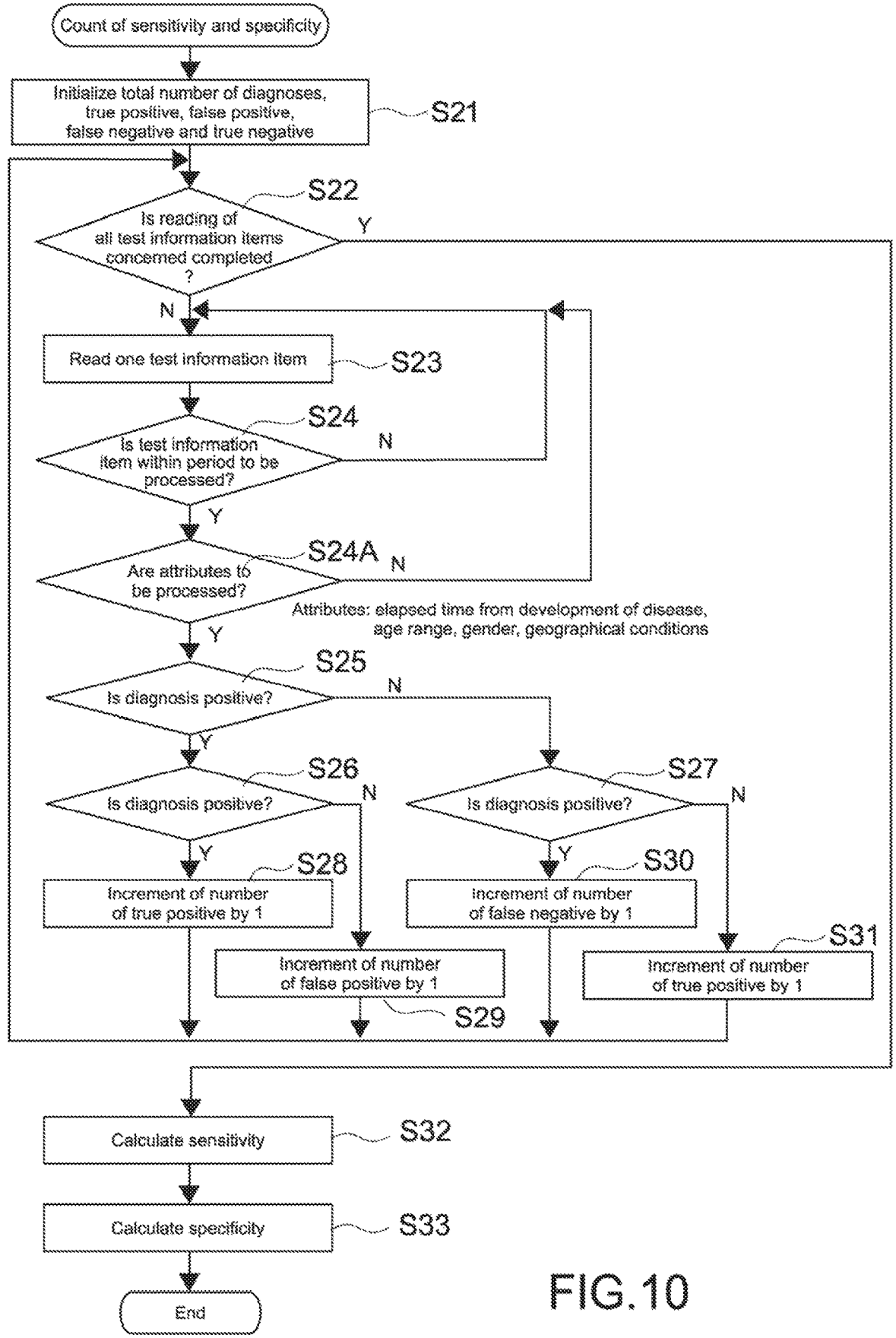
FIG. 10 is a flowchart showing calculation processing (Part 2) of a sensitivity and a specificity by a test server.

FIG. 10 is a flowchart showing calculation processing (Part 2) of a sensitivity and a specificity by a test server 40.

The calculation processing is such that Step S24 is added to the flowchart of the calculation processing shown in FIG. 9.

In Step S24A, whether or not the test information items satisfying that a number of days elapsed is within a predesignated number of days satisfy the predesignated patient attributes.

Here, the predesignated patient attributes include an age range, a gender, geographical conditions, or the like.

The age range of the patients is classified into less than 10, 10s, 20s, for example. Any age range therefrom is provided as one of the predesignated patient attributes.

The geographical conditions include Address (address, administrative district), Country (country) and Belongs (organization, company, other group), for example. Specifically, the geographical conditions may be an area within 50 km from a certain place in radius. Alternatively, the geographical conditions may be a work place where the patient goes frequently or a meeting place of a community as well as the patient address.

Then, the CPU 41 takes out the respective information items of the test result and the diagnosis result included in the test information items, and updates the above-described respective variables used for calculation of the sensitivity and the specificity based on a combination of the information items (Step S25-Step 31).

In this manner, in addition to the number of days elapsed, a sensitivity and a specificity of the age range, a sensitivity and a specificity of the gender, a sensitivity and a specificity of the geographical conditions.

As the patient attributes, an information item about a medical interview, an information item about current and past drug administration, an information item about a past health history, a body temperature, a blood pressure and a body weight, and an information item about life habits such as a degree of exercise, a quantity and a kind of a meal, a sleeping time may be used. In this case, the above-described information items are naturally added as the test information items.

(5. Calculation of Sensitivity and Specificity of Test Method Having Significant Correlation Between Test Result and Diagnosis Result)

Next, calculation processing of a sensitivity and a specificity of a test method narrowed down by a correlation between a test result and a diagnosis result will be described.

When there are a plurality types of the test method for one test subject and accuracy of the sensitivity and the specificity provided for the respective test methods, significant information for selecting a test method by a doctor can be provided.

For example, a test method of a prostate cancer will be simply described. As the test method of a prostate cancer, the PSA test, there are a test by genetic polymorphism analysis, and a tissue test (needle biopsy) using a test device. The result of the test is numerical data. A method of diagnosing the prostate cancer by a doctor includes rectal examination and an ultrasound examination, which is determined by the doctor for positive/negative.

In the embodiment, the CPU 41 determines whether or not there is a significant correlation between a group of numerical data that is the test result and the diagnosis result. The CPU 41 calculates the sensitivity and the specificity in the test method corresponding to the group of numerical data that is determined to have the significant correlation, and adds each item of the test result and the diagnosis result by the test method to a test diagnosis item of the test subject (prostate cancer) thereafter.

Next, the operation will be described in detail by assuming that the test subject is a prostate cancer.

Figure 11:
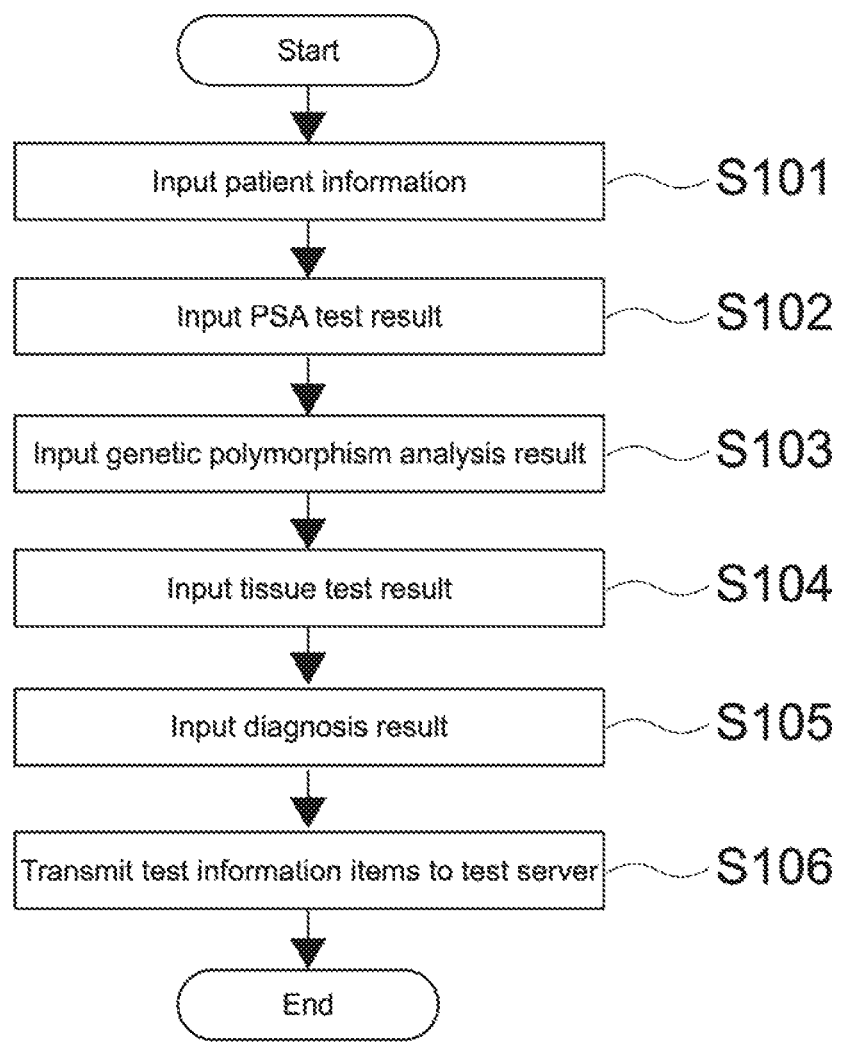
FIG. 11 is a flowchart showing an operation of a test terminal where a test subject is a prostate cancer.

FIG. 11 is a flowchart showing an operation of the test terminal 20 where the test subject is a prostate cancer.

Figure 12:
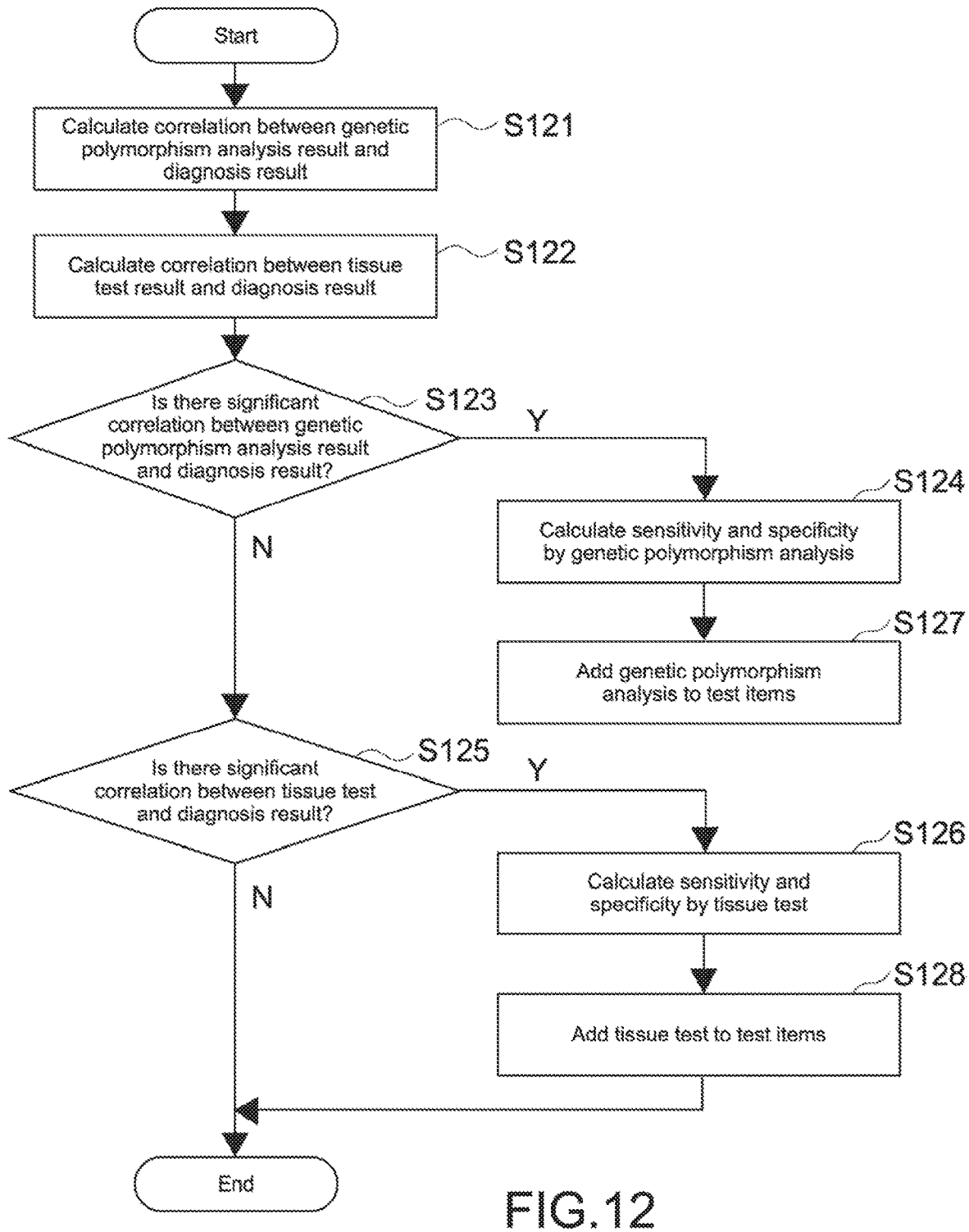
FIG. 12 is a flowchart showing an operation of a test server where a test subject is a prostate cancer.

FIG. 12 is a flowchart showing an operation of the test server 40 where the test subject is a prostate cancer.

As a plurality of the test methods for one test subject (prostate cancer), three types are assumed: the PSA test, the test by genetic polymorphism analysis, and the tissue test (needle biopsy). The result of the test is numerical data. The method of determining the correlation between the test result and the diagnosis result by the doctor includes two types: the test by the genetic polymorphism analysis, and the tissue test (needle biopsy).

The doctor who is the user of the test terminal 20 inputs patient information to the test terminal 20 (Step 101). The doctor inputs the test result by the above-described three test methods to the test terminal 20 (Steps S102, 103, and 104). Thereafter, the doctor performs diagnosis by referring to the test result, and inputs the diagnosis result to the test terminal 20 (Step S105).

Then, the CPU 21 of the test terminal 20 generates test information items including patient information, a test result, and a diagnosis result, transmits them to the test server 40, and causes the database 47a to store them (Step S106).

The CPU 41 of the test server 40 reads one or more of the test result by the genetic polymorphism analysis and the diagnosis result by the doctor corresponding thereto from the test information items stored in the database 47a. The CPU 41 of the test server 40 determines a correlation between the test result by the genetic polymorphism analysis and the diagnosis result (Step S121).

Then, the CPU 41 of the test server 40 reads one or more of the test result by the genetic polymorphism analysis and the diagnosis result by the doctor corresponding thereto from the test information items stored in the database 47a. The CPU 41 of the test server 40 determines a correlation between the diagnosis result by the tissue test (needle biopsy) and the diagnosis result (Step S122).

The CPU 41 of the test server 40 determines whether or not there is a significant correlation between the test result by the genetic polymorphism analysis and the diagnosis result (Step S123). When there is the significant correlation, the CPU 41 of the test server 40 executes the above-described (4. Calculation Processing of Sensitivity and Specificity by Test Server 40 (Part 2)) using the test method of the genetic polymorphism analysis as the condition of a processing subject. In this way, the sensitivity and the specificity in the test method by the genetic polymorphism analysis are calculated (Steps S124).

The CPU 41 of the test server 40 determines whether or not there is a significant correlation between the tissue test (needle blopsy) determined in Step S122 and the diagnosis result (Step S125). When there is the significant correlation, the sensitivity and the specificity in the test method of the tissue test (needle blopsy) are calculated (Step S126).

The correlation can be determined by using an ANOVA (analysis of variance), for example. The ANOVA (analysis of variance) is a method of splitting data changes into meaningless changes corresponding to errors and meaningful changes based on a plurality of standards to determine a variance ratio thereof, and of judging that there are changes due to any factor when the meaningful changes are sufficiently greater than the errors. Specifically, when the factor is the test method and the meaningful changes are generated in the group of quantized test result by the test method, the presence or absence of the significant correlation is determined by the ANOVA (analysis of variance).

When the test method that is judged as having the correlation, the CPU 41 of the test server 40 adds the test method to the test items that are referred upon the determination by the doctor as to a test policy of the prostate cancer to cause more test information items of the test method to collect by the test server 40 (Step S127, S128). This allows the sensitivity and the specificity calculated to be further improved.

As above, the test method of the prostate cancer is illustrated. The present method is also applicable to a plurality of test methods of other test subject.

A correlation between a result of the PSA test and a diagnosis result by the doctor may be determined to calculate the sensitivity and the specificity of the PSA test.

In the above, the correlation between the quantized test result and the diagnosis result is calculated. A correlation between a combination of the quantized test result and the patient's attributes and the diagnosis result may be calculated. For example, a correlation between the test result of the genetic polymorphism analysis "A", the age range "40s or more", the gender "male" and a residence "Japan" and the diagnosis result "presence of disease" may be calculated. This allows an unknown disease factor to be found. Also, when a strain of the test subject is changed every moment, the sensitivity and the specificity can be updated every time.

(Presentation of Superior Test Method to Test Subject)

Figure 13:
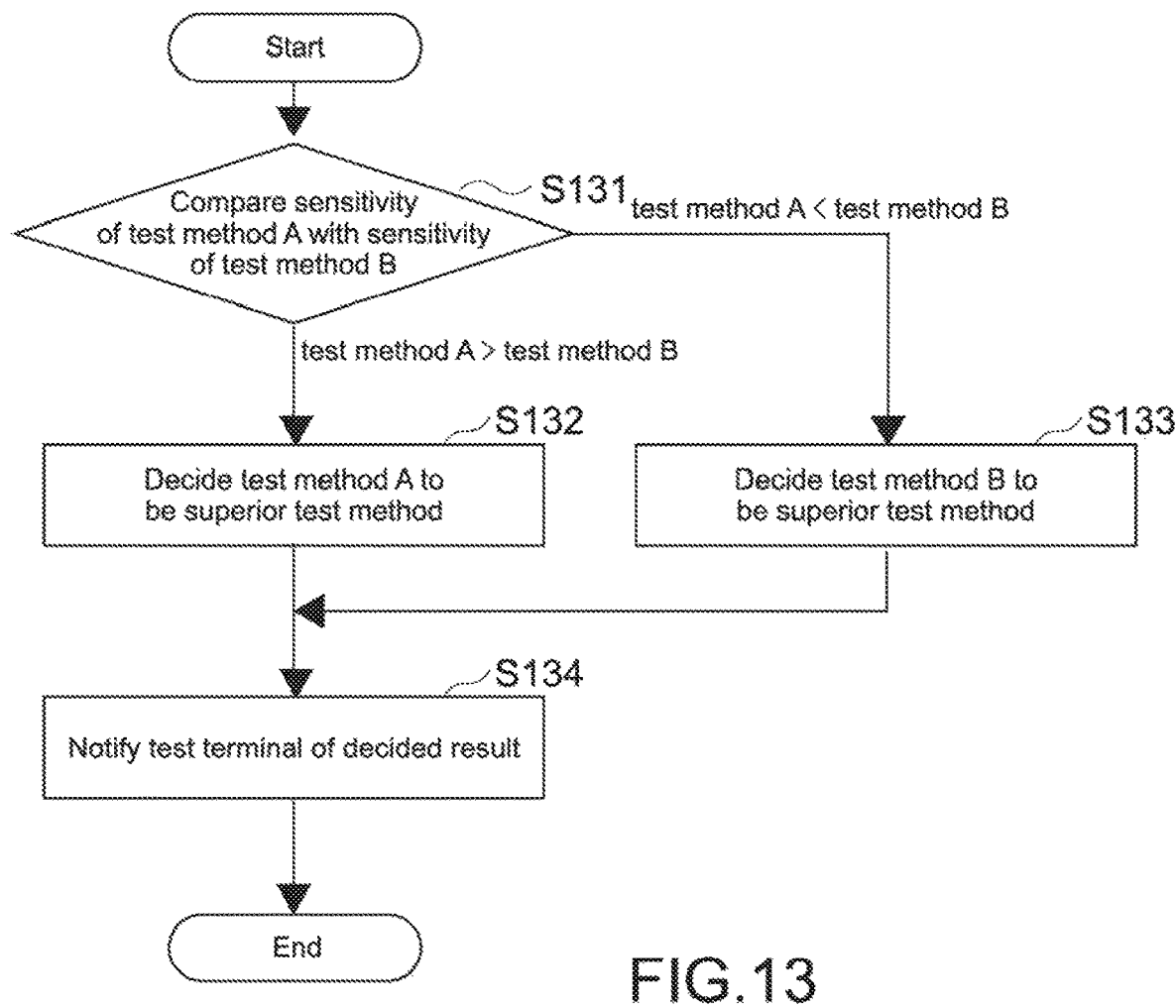
FIG. 13 is a flowchart showing a procedure that a test server presents a superior test method to a test subject.

In this embodiment, as shown in FIG. 13, the CPU 41 of the test server 40 compares the sensitivities calculated for a plurality of the test methods A and B of the same test subject (disease) to determine the test method having the highest sensitivity, for example (Step S131). The test method is decided to be superior test method for the test subject (Steps S132 and 133), and the user of the test terminal 20 is notified of the decided result (Step S134).

For a subject period, a short period such as one week is designated to calculate the sensitivity. While a strain of the test subject is changed every moment, the most superior test method can be recommended to the user each time.

In FIG. 13, the test method recommended is determined based on the sensitivity in order to avoid false negative as a disease feature. Alternatively, determination conditions combined with superiority or inferiority of the specificity may be used.

Also in this case, the CPU 41 of the test server 40 may narrow down the test information items by the patient's attributes such as gender, age range and geographical conditions predesignated to calculate the sensitivity and the specificity.

(7. Setting of Cut-Off Value where Sensitivity and Specificity are Superior)

Figure 14:
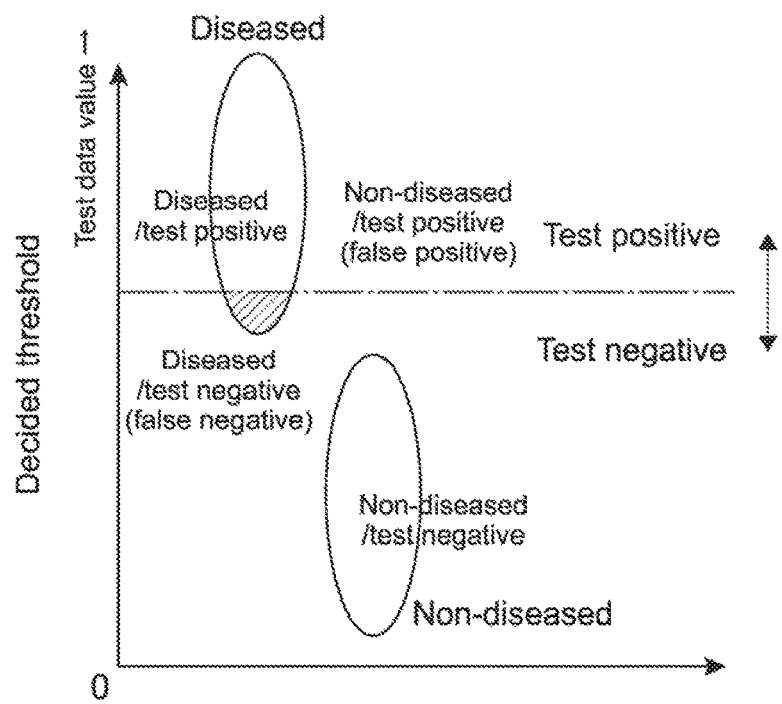
FIG. 14 is a diagram for describing a threshold value for evaluating a quantized test result.

For the quantized test result, it is ideal to split into diseased patient groups and non-diseased patient groups by a certain threshold value, as shown in FIG. 14.

Figure 15:
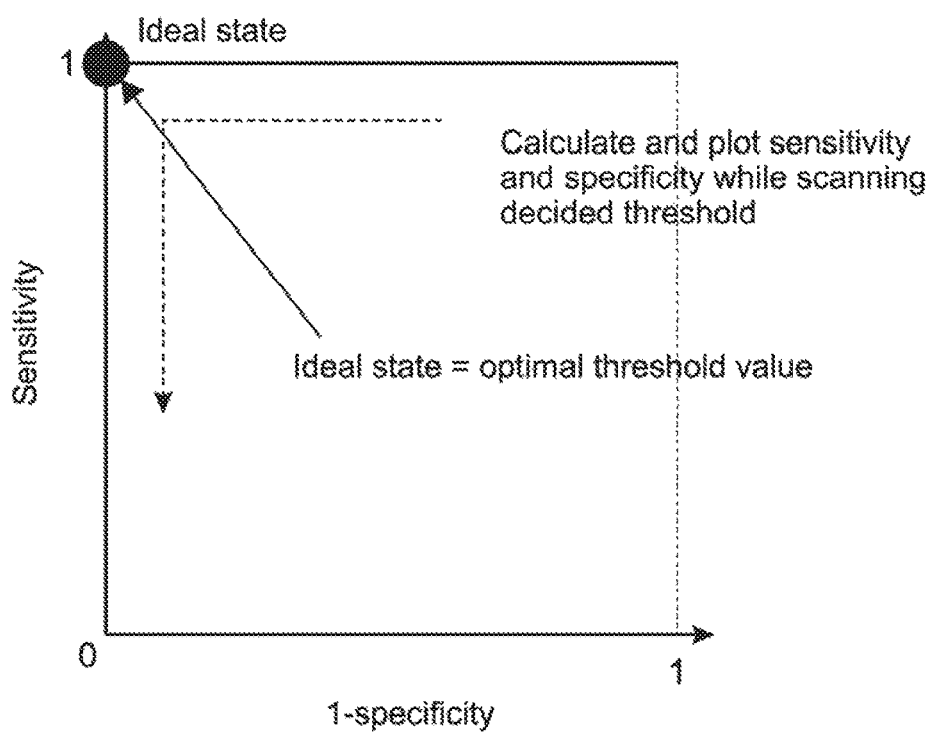
FIG. 15 is a diagram showing a ROC diagram corresponding to FIG. 14.

There is a technique named ROC (Receiver Operator Characteristic) diagram. As shown in FIG. 15, the ROC diagram is a plot of the sensitivity and a "1−specificity" that are calculated by shifting the threshold value by one step. In FIG. 14, there is an optimal threshold value that can split into the diseased patient groups and the non-diseased patient groups.

Figure 16:
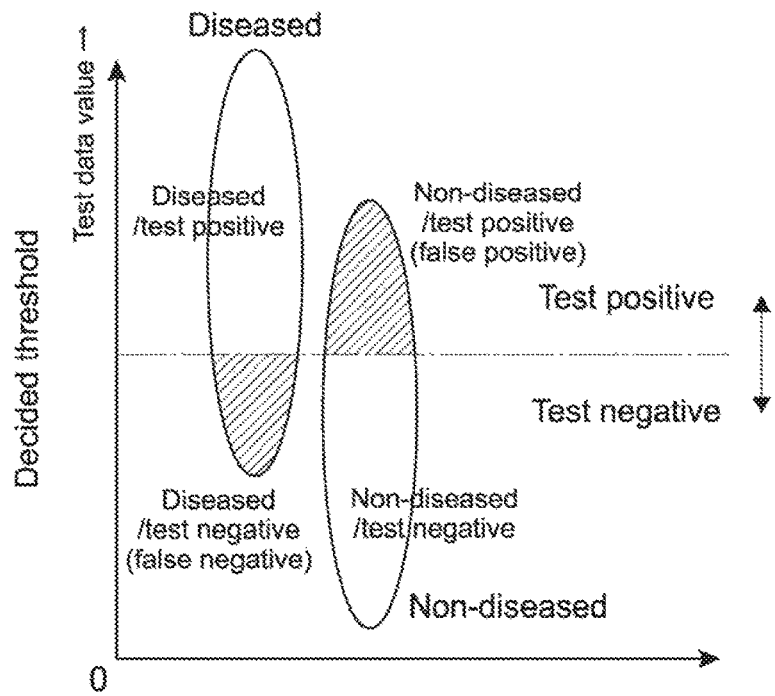
FIG. 16 is a diagram for describing a practical threshold value.
Figure 17:
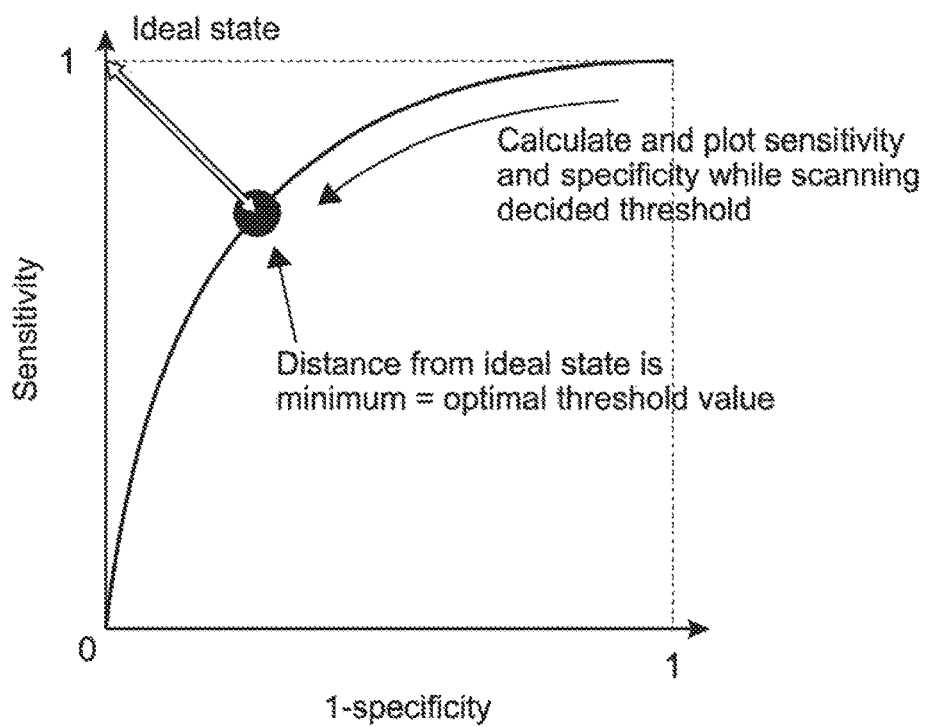
FIG. 17 is a diagram showing a ROC diagram corresponding to FIG. 16.

In reality, as shown in FIG. 16, the diseased patient groups and the non-diseased patient groups are often not split by a single threshold value. FIG. 17 is a ROC diagram that the diseased patient groups and the non-diseased patient groups are not split by a single threshold value.

In the ROC diagram in FIG. 17, the optimal threshold value is corresponding to the position where the distance from an ideal state is a minimum.

Figure 18:
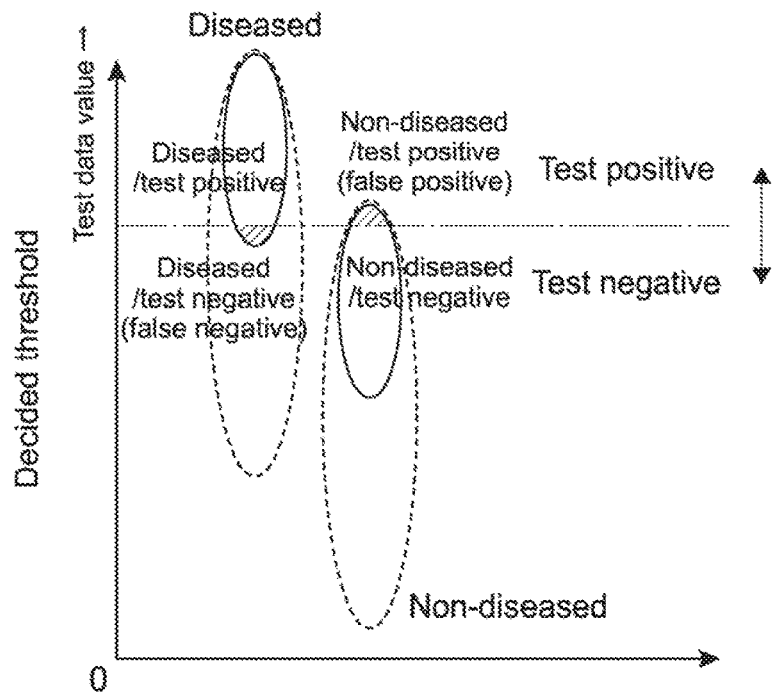
FIG. 18 is a diagram for describing a threshold value when grouping by attribute information.
Figure 19:
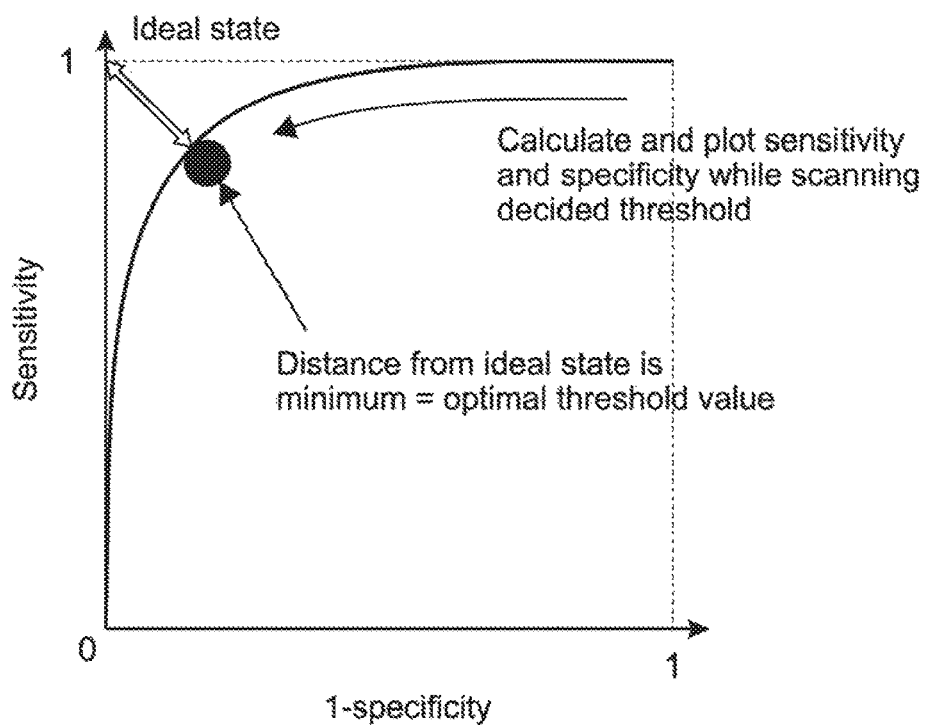
FIG. 19 is a diagram showing a ROC diagram corresponding to FIG. 18.

In contrast, as shown in FIG. 18, when the test data items are grouped by certain patient attribute, the threshold value closer to the ideal state may be provided as shown in FIG. 19.

Figure 20:
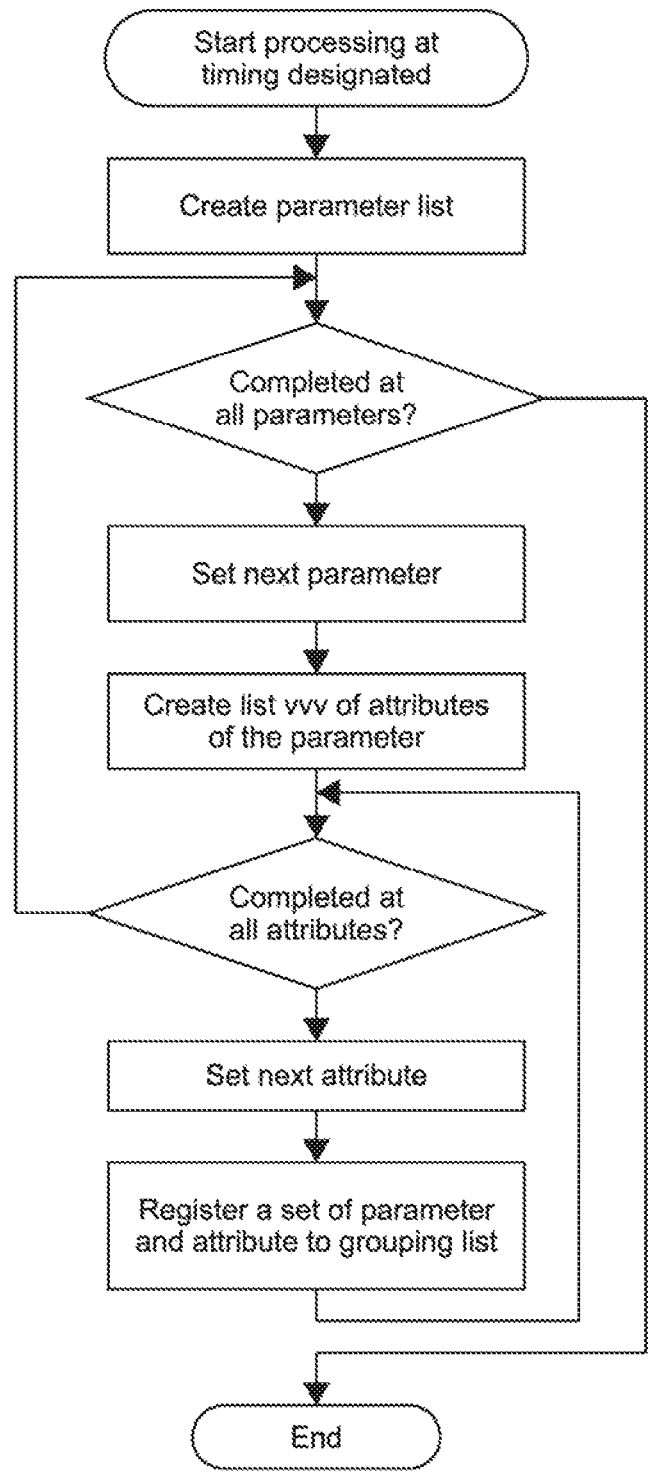
FIG. 20 is a flowchart showing a procedure for creating a grouping list of test data items.
Figure 21:
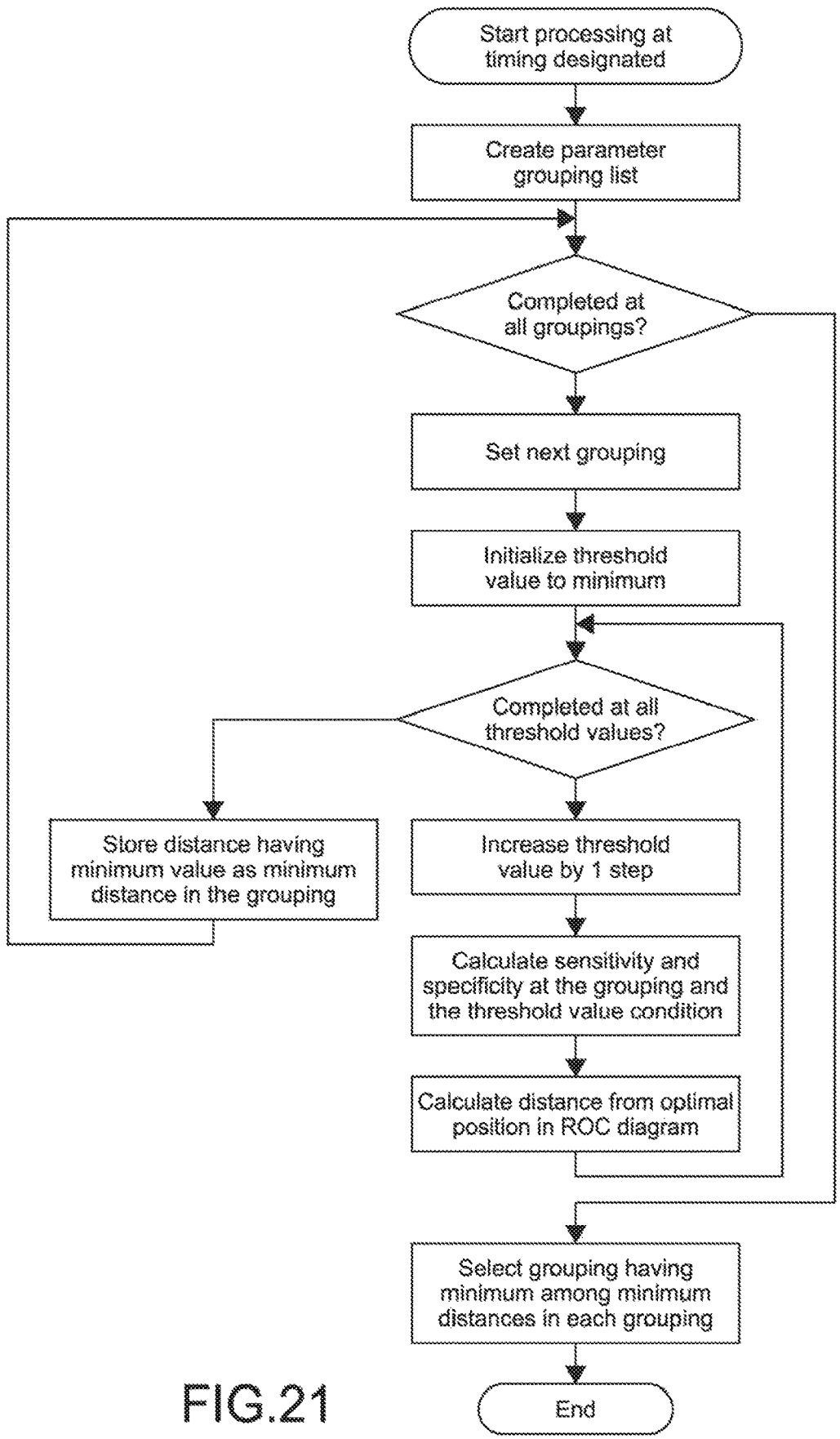
FIG. 21 is a flowchart showing a procedure for calculating a threshold value for each group from a grouping list of test data items.

FIG. 20 is a flowchart showing a procedure for creating a grouping list of test data items. FIG. 21 is a flowchart showing a procedure for calculating a threshold value for each group from a grouping list of test data items.

As shown in FIG. 19, the CPU 41 of the test server 40 reads the test data item that satisfies the patient attribute predesignated from the test result database 47a, and registers it to the grouping list as the test data item belonging to one group. Similarly, the CPU 41 of the test server 40 reads the test data item that satisfies another predesignated patient attribute, and registers it to the grouping list as the test data item belonging to another group. The processing is repeated for the predesignated patient attribute. In this manner, the grouping list of the test data items is created.

Next, to the grouping list of the test data items created, the CPU 41 of the test server 40 calculates the sensitivity and the "1−specificity" by changing the threshold value by one step to determine a minimum value of a distance from an ideal state in the respective groups. Then, the CPU 41 of the test server 40 sets the minimum value from the minimum values of the distance from the ideal state in the respective groups as a cut-off value where the sensitivity and the specificity are superior.

In the above description, the optimal threshold value per group is such that the distance from the ideal state is the minimum value in the ROC diagram. Alternatively, the optimal threshold value per group may be determined by other method.

In the above description, the minimum value among the optimal threshold values in the respective groups is set to the cut-off value where the sensitivity and the specificity are superior. However, the present technology is not limited thereto. The value selected from other method may be set to the cut-off value.

The grouping list is created for one type of the test data item as a subject, but may be created for a combination of a plurality types of the test data items as the subject.

One value (minimum value) from the optimal threshold values in the respective groups is set. A plurality of values from the optimal threshold values in the respective groups may be used to split the presence or absence of the disease.

Figure 22:
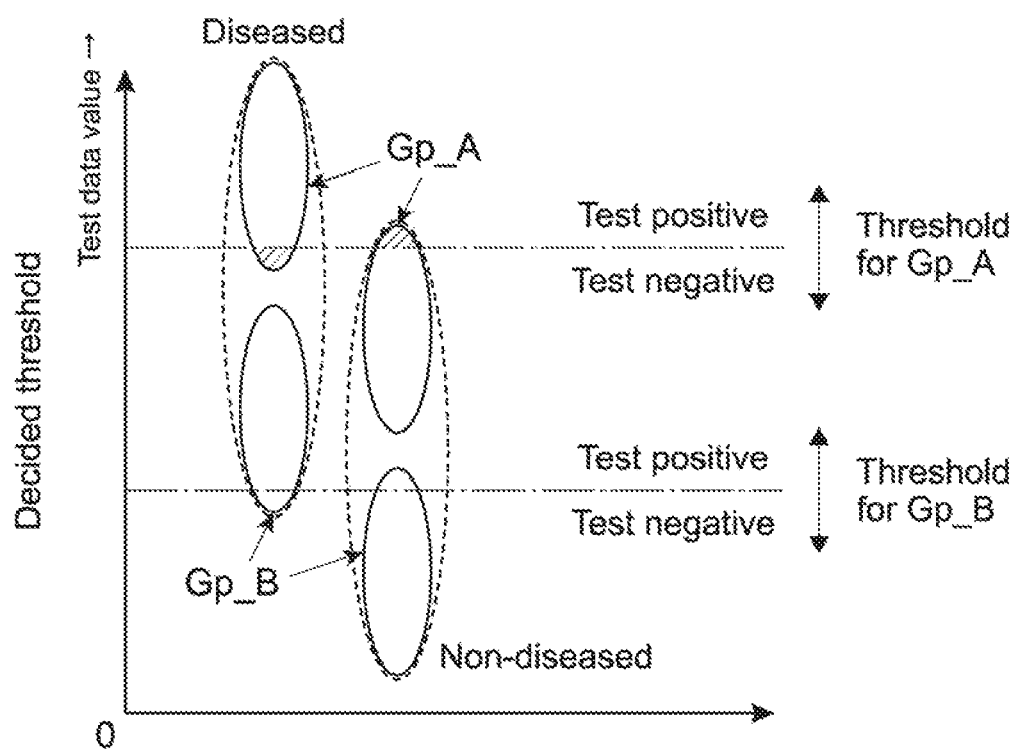
FIG. 22 is a diagram for describing a method of splitting into the presence or absence of the disease using a best threshold value number for each of a plurality of groups.

For example, as shown in FIG. 22, it is assumed that an optimal threshold value of a group Gp_A and an optimal threshold value of a group Gp_B are set. In this case, the test subject (patient) exceeding the optimal threshold value is regarded as having the disease in any group. In this manner, the test is possible at the sensitivity and the specificity superior than that using the single threshold value.

[Regarding Effects by the Embodiment]

By the test system 10 according to this embodiment, for example, the following effects can be obtained.

The sensitivity and the specificity of the test kit can be provided not only when the test kit is clinically developed, but also based on actual test performance after postmarketing. In this manner, health personnels can be provided with latest, accurate and real information about the performance of the sensitivity and the specificity of the test kit that is deviated from the actual. As a result, a doctor can diagnose more accurately.

The test kit that is deviated from the actual is, for example, a kit for a disease as follows:

1. A changing infectious disease, e.g., Influenza virus. The sensitivity and the specificity of the test subject diseased are changed depending on the season when the test kit is used.
2. A disease where a number of genetic polymorphisms are involved and relevant genetic polymorphisms are newly found.
3. A disease where an environmental factor is polymorphically involved as well as a genetic factor.

[Supplementary Note]

In addition, the present technology is not limited to the above embodiments and can be variously modified without departing from the gist of the present technology as a matter of course.

[Another Configuration of the Present Technology]

It should be noted that the present technology can have the following configurations.

(1) A test server, including:

a communication unit that communicates with a plurality of communication terminals via a network, the plurality of communication terminals each being capable of inputting a test result on the presence or absence of the disease and a diagnosis result about the presence or absence of the disease being related to the test and made by a doctor; and a control unit that acquires test information items including at least the test result and the diagnosis result from the plurality of communication terminals via the communication unit, causes a storage unit to store the plurality of acquired test information items therein, calculates at least one of a sensitivity and a specificity of the test by statistical processing of the plurality of stored test information items, and causes the communication unit to respond to a result of the statistical processing according to a demand given from each of the communication terminals.

(2) The test server according to (1) above, in which the test information items further include an information item about an elapsed time from a development of a disease, and the control unit calculates at least one of the sensitivity and the specificity of the test by statistical processing of the test information item about an elapsed time from a development of a disease predesignated.

(3) The test server according to (1) or (2) above, in which the test information items include quantized test data items as the test results, and the control unit groups the test data items for each attribute of the patient, calculates a sensitivity and a specificity by changing a threshold value for splitting into the presence or absence of the disease, and calculates the threshold value based on the sensitivity and the specificity.

(4) The test server according to any one of (1) to (3) above, in which the control unit compares at least one of the sensitivity and the specificity of a plurality types of tests performed on the same test subject, and determines a superior type of the test for the test subject.

(5) The test server according to any one of (1) to (4) above, in which the control unit calculates at least one of a positive likelihood ratio and a negative likelihood ratio, and cause the communication unit to respond thereto.

DESCRIPTION OF SYMBOLS 10 test system
20 test terminal

21 CPU
22 ROM
23 RAM
24 operation input unit
25 network interface unit
26 display unit
27 storage unit
28 test device
30 network (Internet)
40 test server
41 CPU
42 ROM
43 RAM
44 operation input unit
45 network interface unit
46 display unit
47 storage unit
47a database 47a

The invention claimed is:

1. A test server, comprising:
a memory; and
one or more processors configured to:
communicate with a plurality of communication terminals via a network, wherein each communication terminal of the plurality of communication terminals is configured to:
input a test result of a test by genetic polymorphism analysis on one of a presence or an absence of a disease of a patient; and
input a diagnosis result for one of the presence or the absence of the disease, wherein the diagnosis result is related to the test and is made by a doctor; and
acquire a plurality of test information items from the plurality of communication terminals via the network, wherein the plurality of test information items includes the diagnosis result and quantized test data items as the test result;
store the acquired plurality of test information items in the memory;
group the quantized test data items for each attribute of the patient;
determine the presence or the absence of the disease in each group of the quantized test data items based on a first threshold value of a plurality of threshold values;
calculate a first value of sensitivity and a first value of specificity of the test based on the first threshold value for each group of the quantized test data items;
change the first threshold value to a second threshold value of the plurality of threshold values for the determination of the presence or the absence of the disease in each group of the quantized test data items;
calculate a second value of the sensitivity and a second value of the specificity of the test based on the second threshold value for each group of the quantized test data items;
determine the second threshold value as an optimal threshold value among the plurality of threshold values for each group of the quantized test data items, wherein the second threshold value is based on a minimum distance from an ideal state to a position on a plot of the sensitivity and the specificity;
determine a prevalence rate of the disease, repeatedly at a time period, based on the acquired plurality of test information items;
determine a positive predictive value and a negative predictive value, based on the determined value of the prevalence rate in a most recent time period, the second value of the sensitivity and the second value of the specificity that correspond to the second threshold value;
control transmission of a response to a result of the determination of the positive predictive value and the negative predictive value based on a demand from each communication terminal of the plurality of communication terminals, wherein the response comprises at least one of the positive predictive value or the negative predictive value of the test; and
control transmission of a recommendation for the test, based on the determined negative predictive value and the determined value of the prevalence rate in the most recent time period.

2. The test server according to claim 1, wherein
the plurality of test information items further includes patient attribute information, and
the one or more processors are further configured to calculate the sensitivity and the specificity of the test based on the plurality of test information items that satisfies designated attributes.

3. The test server according to claim 1, wherein the one or more processors are further configured to:
compare the sensitivity and the specificity of a plurality types of tests performed on a test subject, wherein the plurality of types of tests includes the test; and
determine a specific type of test from the plurality types of tests for the test subject based on the comparison.

4. The test server according to claim 1, wherein the one or more processors are further configured to:
calculate a positive likelihood ratio and a negative likelihood ratio; and
control transmission of the calculated positive likelihood ratio and the negative likelihood ratio.

5. A test method, comprising:
communicating, by one or more processors, with a plurality of communication terminals via a network, wherein each communication terminal of the plurality of communication terminals is configured to:
input a test result of a test by genetic polymorphism analysis on one of a presence or an absence of a disease of a patient; and
input a diagnosis result for one of the presence or the absence of the disease, wherein the diagnosis result is related to the test and is made by a doctor;
acquiring, by the one or more processors, a plurality of test information items from the plurality of communication terminals via the network, wherein the plurality of test information items includes the diagnosis result and quantized test data items as the test result;
storing, by the one or more processors, the acquired plurality of test information items in a memory;
grouping, by the one or more processors, the quantized test data items for each attribute of the patient;
determining, by the one or more processors, the presence or the absence of the disease in each group of the quantized test data items based on a first threshold value of a plurality of threshold values;

calculating, by the one or more processors, a first value of sensitivity and a first value of specificity of the test based on the first threshold value for each group of the quantized test data items;

changing, by the one or more processors, the first threshold value to a second threshold value of the plurality of threshold values for the determination of the presence or the absence of the disease in each group of the quantized test data items;

calculating, by the one or more processors, a second value of the sensitivity and a second value of the specificity of the test based on the second threshold value for each group of the quantized test data items;

determining, by the one or more processors, the second threshold value as an optimal threshold value among the plurality of threshold values for each group of the quantized test data items, wherein the second threshold value is based on a minimum distance from an ideal state to a position on a plot of the sensitivity and the specificity;

determining, by the one or more processors, a prevalence rate of the disease, repeatedly at a time period, based on the acquired plurality of test information items;

determining, by the one or more processors, a positive predictive value and a negative predictive value, based on the determined value of the prevalence rate in a most recent time period, the second value of the sensitivity and the second value of the specificity that correspond to the second threshold value;

controlling, by the one or more processors, transmission of a response to a result of the determination of the positive predictive value and the negative predictive value based on a demand from each communication terminal of the plurality of communication terminals, wherein the response comprises at least one of the positive predictive value or the negative predictive value of the test; and controlling, by the one or more processors, transmission of a recommendation for the test, based on the determined negative predictive value and the determined value of the prevalence rate in the most recent time period.

6. A test system, comprising:
a plurality of communication terminals; and
a test server, wherein
each communication terminal of the plurality of communication terminals includes an input unit,
the input unit is configured to:
input a test result of a test by genetic polymorphism analysis on one of a presence or an absence of a disease of a patient; and
input a diagnosis result for one of the presence or the absence of the disease, wherein the diagnosis result is related to the test and is made by a doctor, and
the test server comprises:
one or more processors; and
a memory,
wherein the one or more processors are configured to:
communicate with the plurality of communication terminals via a network;
acquire a plurality of test information items from the plurality of communication terminals, wherein the plurality of test information items includes the diagnosis result and quantized test data items as the test result;
store the acquired plurality of test information items in the memory;
group the quantized test data items for each attribute of the patient;
determine the presence or the absence of the disease in each group of the quantized test data items based on a first threshold value of a plurality of threshold values;
calculate a first value of sensitivity and a first value of specificity of the test based on the first threshold value for each group of the quantized test data items;
change the first threshold value to a second threshold value of the plurality of threshold values for the determination of the presence or the absence of the disease in each group of the quantized test data items;
calculate a second value of the sensitivity and a second value of the specificity of the test based on the second threshold value for each group of the quantized test data items;
determine the second threshold value as an optimal threshold value among the plurality of threshold values for each group of the quantized test data items, wherein the second threshold value is based on a minimum distance from an ideal state to a position on a plot of the sensitivity and the specificity;
determine a prevalence rate of the disease, repeatedly at a time period, based on the acquired plurality of test information items;
determine a positive predictive value and a negative predictive value, based on the determined value of the prevalence rate in a most recent time period, the second value of the sensitivity and the second value of the specificity that correspond to the second threshold value; and
control transmission of a response to a result of the determination of the positive predictive value and the negative predictive value based on a demand from each communication terminal of the plurality of communication terminals, wherein the response comprises at least one of the positive predictive value or the negative predictive value of the test; and
control transmission of a recommendation for the test, based on the determined negative predictive value and the determined value of the prevalence rate in the most recent time period.

7. The test server according to claim 1, wherein the positive predictive value and the negative predictive value are indices to identify a probability of one of the presence or the absence of the disease.

* * * * *